(12) United States Patent
Otsuka et al.

(10) Patent No.: US 8,658,735 B2
(45) Date of Patent: Feb. 25, 2014

(54) POLYMERIZABLE MONOMER, GRAFT COPOLYMER, AND SURFACE MODIFIER

(75) Inventors: Hidenori Otsuka, Tokyo (JP);
Masayuki Fukaishi, Narashino (JP);
Takashi Ishiduka, Matsudo (JP)

(73) Assignee: Tokyo University of Science Educational Foundation Administrative Organization, Tokyo (JP)

( * ) Notice: Subject to any disclaimer, the term of this patent is extended or adjusted under 35 U.S.C. 154(b) by 0 days.

(21) Appl. No.: 13/060,582

(22) PCT Filed: Aug. 28, 2009

(86) PCT No.: PCT/JP2009/065119
§ 371 (c)(1),
(2), (4) Date: May 13, 2011

(87) PCT Pub. No.: WO2010/024412
PCT Pub. Date: Mar. 4, 2010

(65) Prior Publication Data
US 2011/0269905 A1 Nov. 3, 2011

(30) Foreign Application Priority Data

Aug. 28, 2008 (JP) ................................. 2008-220573
Sep. 8, 2008 (JP) ................................. 2008-230337

(51) Int. Cl.
*C08G 69/00* (2006.01)
*C08F 26/02* (2006.01)
*C08F 8/32* (2006.01)
*C07D 263/08* (2006.01)

(52) U.S. Cl.
USPC .............. 525/55; 526/263; 525/375; 548/237

(58) Field of Classification Search
USPC ...................... 525/375, 55; 526/263; 560/160; 564/391, 504, 15; 548/237
See application file for complete search history.

(56) References Cited

U.S. PATENT DOCUMENTS

2008/0207913 A1* 8/2008 Breitenkamp et al. ........ 548/237

FOREIGN PATENT DOCUMENTS

| CH | 476762 | 8/1969 |
|---|---|---|
| EP | 550998 | 7/1993 |
| JP | 2009-149903 | 7/2009 |
| WO | 2006/047419 | 5/2006 |
| WO | 2007/120579 | 10/2007 |
| WO | 2007/127473 | 11/2007 |

OTHER PUBLICATIONS

Tomomi Satomi et al. (Journal of Nanoscience and Nanotechnology, vol. 6, 1792-1796, 2006).*
W. Peter Wuelfing, Stephen M. Gross, Deon T. Miles, and Royce W. Murray; Journal of American Chemical Society; 1998; 120(48); pp. 12696-12697.
Hidenori Otsuka, Yoshitsugu Akiyama, Yukio Nagasaki, and Kazunori Kataoka; Journal of American Chemical Society; 2001; 123(34); pp. 8226-8230.
Tomomi Satomi, Koji Ueno, Yohei Fujita, Hisatoshi Kobayashi, Junzo Tanaka, Yoshinori Mitamura, Tetsuya Tateishi, and Hidenori Otsuka; Journal of Nanoscience and Nanotechnology; 2006; 6; pp. 1792-1796.
Tomomi Satomi, Koji Ueno, Yohei Fujita, Hisatoshi Kobayashi, Tetsuya Tateishi, and Hidenori Otsuka; "Characteriztion of Polypyridine-graft-PEG Copolymer at Interface"; Journal of the Japan Society of Colour Material, 2006; 79(11); pp. 475-485(1).
Masayuki Fukaishi, Yohei Fujita, Tomomi Satomi, Koji Ueno, and Hidenori Otsuka; Interfacial Characterization of Poly(vinyl pyridine)-graft-Poly(ethelene glycol)(Py-g-PEG); Polymer Preprints, Japan (CD-ROM); 2007; 56(1); Disk 1; 1PH096.
Takashi Ishiduka, Michihiro Iijima, Koji Ueno, and Hidenori Otsuka; "Synthesis of Polypyridine-graft-functional PEG Copolymer and Their Interfacial Characterization"; Polymer Preprints, Japan (CD-ROM); 2008; 57(2); Disk 1; 2PF068.
Satomi T et al: "Synthesis of polypyridine-graft-PEG copolymer for protein repellent and stable interface", Journal of Nanoscience and Nanotechnology, American Scienliflc Publishers, vol. 6, No. 6, Jun. 1, 2006, pp. 1792-1796, XP009155532, ISSN: 1533-4880, DOI: 10.1166/JNN.2006.234.
Supplementary European Search Report issued to EP Application No. 09810060.5, mailed Jan. 27, 2012.

\* cited by examiner

*Primary Examiner* — Liam Heincer
*Assistant Examiner* — Marilou Lacap
(74) *Attorney, Agent, or Firm* — Dilworth & Barrese, LLP.

(57) ABSTRACT

The graft copolymer comprises a polymerizable monomer (A1) represented by general formula (III) and a polymerizable monomer (B1) containing a pyridyl group, and a ligand can be bonded via the functional group at the terminus of $R^{3a}$. In the formula, $R^{1a}$ represents a polymerizable group, $R^{2a}$ represents an alkylene group having a carbon number of 2-5, $R^{3a}$ represents an organic group having at a terminus a functional group selected from among an azide group, a phenyl azide group, a carboxyl group, a primary to quaternary amino group, an acetal group, an aldehyde group, a thiol group, a disulfide group, an active ester group, a trialkoxysilyl group, and a polymerizable group, and n represents any integer from 5 to 20,000.

(III)

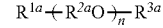

13 Claims, 20 Drawing Sheets

POLYMERIZABLE MONOMER, GRAFT COPOLYMER, AND SURFACE MODIFIER

TECHNICAL FIELD

The present invention relates to a polymerizable monomer, a method for producing the same, and a graft copolymer between the polymerizable monomer and other polymerizable monomers. The present invention also relates to a surface modifier, an object which has been modified with the surface modifier, a dispersion of nanoparticles which have been modified with the surface modifier, and a method for producing nanoparticles using hydrophobic cores of micelles formed from the surface modifier as a reaction field.

BACKGROUND ART

In recent years, surface modification of materials has been widely challenged in order to enhance an added value of the materials in a variety of fields. Particularly, fine particles which have been prepared by processing a material to a nanoscale (hereinafter, referred to as "nanoparticles") have a very large specific surface area, the surface properties of which can be readily modified, and thus their affinity, adhesive property in living bodies, etc. can be controlled; therefore, it is anticipated that the fine particles will find application in catalysts, color materials, electronic materials, optical materials, medical supplies, cosmetic products, etc.

Among such nanoparticles, gold nanoparticles have a characteristic property of producing a bright pink color by surface plasmon absorption when in a dispersed state and changing the color hue to purple when in an aggregated state. Therefore, gold nanoparticles have been actively challenged for their applications in biotechnology fields through stably dispersing the gold nanoparticles and functionalizing the surface thereof.

A thiolated poly(ethylene glycol) (PEG-SH) has heretofore been reported by Murray et al. (see Non-Patent Document 1) to be a dispersant capable of stably dispersing gold nanoparticles. On the other hand, the present inventors have developed and reported a poly(ethylene glycol) (hetero PEG) having a thiol group with higher coordination ability to surface of gold at one terminus and a functional group for introducing a ligand at another terminus (see Non-Patent Document 2). If various ligands such as antibodies, oligo DNAs, and sugars (sugar chain) are introduced into the hetero PEG, the gold nanoparticles are provided with the ligands on their dispersed surface and thus will be utilized as practicable diagnosing or analyzing nanoparticles.

Incidentally, it is necessary for the purpose of stably dispersing nanoparticles as an object to be modified to a satisfactory level that the above-mentioned thiols coat the surface of particles more densely than polymers functional as a multidentate ligand since the thiols are a monodentate ligand. Therefore, it will also be preferred if multipoint adsorption and stabilization can be achieved by grafting a polymerizable monomer having a thiol group. However, the high reactivity of the thiol group easily leads to deprotection and cross-linking even if the polymerizable monomer has a terminal protective group, therefore, it is difficult to graft polymerizable monomers having a thiol group.

Then, the present inventors have investigated to find that the graft copolymer between the polymerizable monomer (A) represented by general formula (I) and the polymerizable monomer (B) represented by general formula (II) is useful as a polymeric molecular structure of a surface modifier (see Non-Patent Document 3).

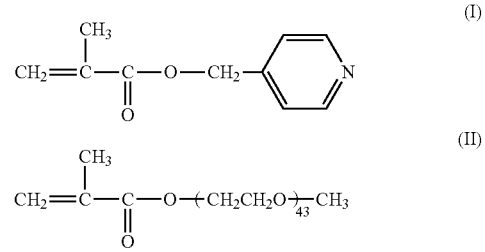

However, in accordance with the above-mentioned finding, the surface of gold nanoparticles could not be functionalized even if the gold nanoparticles can be more stably dispersed since a pyridyl group undergoes multipoint coordination on the surface of the gold nanoparticles.

[Non-Patent Document 1] W. Peter Wuelfing, S. M. G., Deon T. Miles, Royce W. Murray; Journal of American Chemical Society; 1998; 120(48); pp. 12696-12697.

[Non-Patent Document 2] Hidenori Otsuka, Y. A., Yukio Nagasaki, Kazunori Kataoka; Journal of American Chemical Society; 2001; 123(34); pp. 8226-8230.

[Non-Patent Document 3] Tomomi Satomi, Koji Ueno, Hisatoshi Kobayashi, Junzo Tanaka, Yoshinori Mitamura, Tetsuya Tateishi, and Hidenori Otsuka, Journal of Nanoscience and Nanotechnology, 2006; 6, pp. 1792-1796.

DISCLOSURE OF THE INVENTION

Problems to be Solved by the Invention

The present invention has been made in view of the problems described above; and it is an object of the present invention to provide a polymerizable monomer used for a graft copolymer which can multipoint-coordinate on a surface of a material as an object to be modified, and functionalize the surface thereof, a method for producing the polymerizable monomer, and a graft copolymer between the polymerizable monomer and other polymerizable monomers.

It is also an object of the present invention to provide a surface modifier which can exhibit high affinity to an object to be modified and can stably disperse the object to be modified in a solvent by adsorbing onto the surface of the object to be modified, an object which has been modified with the surface modifier, a dispersion of nanoparticles which have been modified with the surface modifier, and a method for producing nanoparticles using hydrophobic cores of micelles formed from the surface modifier as a reaction field.

Means for Solving the Problems

The present inventors have thoroughly investigated to attain the object described above, thereby completing the present invention as follows:

In a first aspect of the present invention, a polymerizable monomer is represented by general formula (III).

(In the formula, $R^{1a}$ represents a polymerizable group, $R^{2a}$ represents an alkylene group having a carbon number of 2-5, $R^{3a}$ represents an organic group having at a terminus a functional group selected from among an azide group, a phenyl azide group, a carboxyl group, a primary to quaternary amino group, an acetal group, an aldehyde group, a thiol group, a disulfide group, an active ester group, a trialkoxysilyl group, and a polymerizable group, and n represents any integer from 5 to 20,000.)

According to a second aspect of the present invention, in the polymerizable monomer according to the first aspect, $R^{1a}$ is a group expressed by general formula (IV).

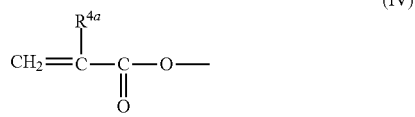

(IV)

(In the formula, $R^{4a}$ is a hydrogen atom or an alkyl group having a carbon number of 1-10.)

According to a third aspect of the present invention, the polymerizable monomer according to the first or second aspect has a weight-average molecular weight from 200 to 80,000.

In a fourth aspect of the present invention, a method for producing a polymerizable monomer represented by formula (8) includes the steps from (a) to (e) in sequence.

(a) A first step of protecting a hydroxyl group at one terminus of ethylene glycol represented by formula (1) with a tetrahydropyranyl group to prepare the compound represented by formula (2).

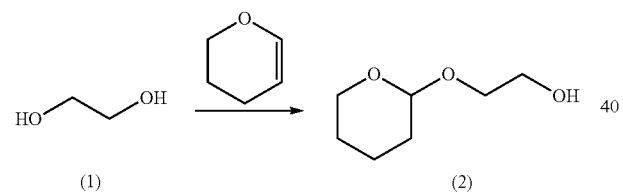

(b) A second step of reacting the compound represented by formula (2) and ethylene oxide to prepare the compound represented by formula (3).

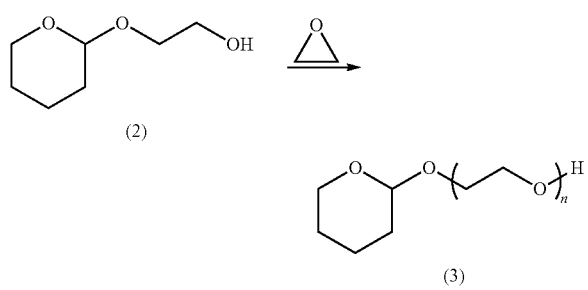

(In the formula, n represents any integer from 5 to 2,000.)

(c) A third step of reacting the compound represented by formula (3) and the compound represented by formula (4) to prepare the compound represented by formula (5).

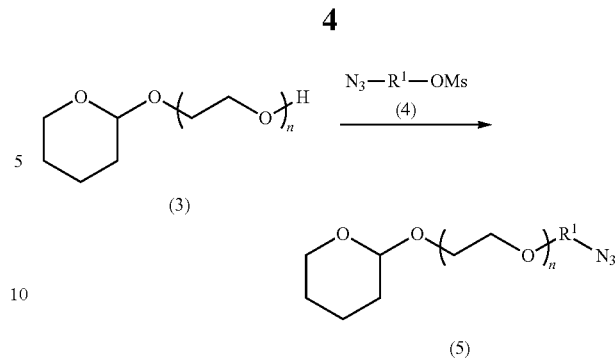

(In the formula, $R^1$ represents an alkylene group having a carbon number of 1-10, and Ms represents a mesyl group.)

(d) A fourth step of deprotecting the tetrahydropyranyl group of the compound represented by formula (5) to prepare the compound represented by formula (6).

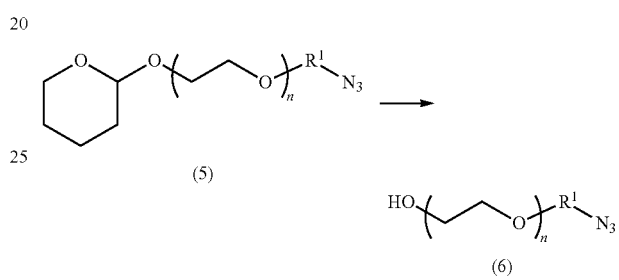

(e) A fifth step of reacting the compound represented by formula (6) and the compound represented by formula (7) to prepare the compound represented by formula (8).

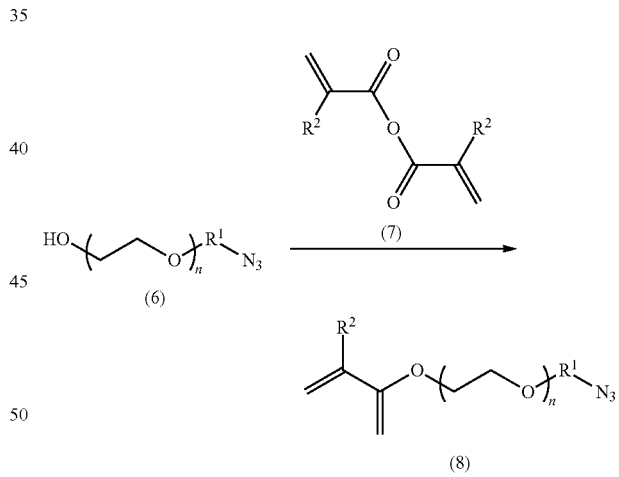

(In the formula, $R^2$ is a hydrogen atom or an alkyl group having a carbon number of 1-10.)

In a fifth aspect of the present invention, a graft copolymer between a polymerizable monomer (A1) represented by general formula (III) and a polymerizable monomer having a pyridyl group (B1) is provided.

(III)

(In the formula, $R^{1a}$ represents a polymerizable group, $R^{2a}$ represents an alkylene group having a carbon number of 2-5, $R^{3a}$ represents an organic group having at the terminus a functional group selected from among an azide group, a phenyl azide group, a carboxyl group, a primary to quaternary amino group, an acetal group, an aldehyde group, a thiol group, a disulfide group, an active ester group, a trialkoxysilyl group, and a polymerizable group, and n represents any integer from 5 to 20,000.)

According to a sixth aspect of the present invention, in the graft copolymer according to the fifth aspect, the polymerizable monomer (B1) is represented by general formula (V).

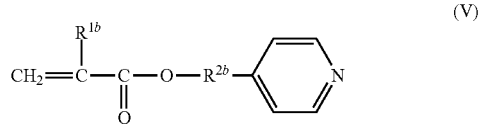
(V)

(In the formula, $R^{1b}$ represents a hydrogen atom or an alkyl group having a carbon number of 1-10, and $R^{2b}$ represents an alkylene group having a carbon number of 1-7.)

According to a seventh aspect of the present invention, in the graft copolymer according to the fifth or sixth aspect, the mole ratio of the polymerizable monomer (A1) to the polymerizable monomer (B1) is from 1:99 to 99:1.

According to an eighth aspect of the present invention, in the graft copolymer according to any one of the fifth to seventh aspects, a ligand is bonded via a functional group at a terminus of $R^{3a}$ in general formula (III).

In a ninth aspect of the present invention, a modified object includes an object which has been modified by adsorbing onto a surface thereof the graft copolymer according to any one of the fifth to eighth aspects.

In a tenth aspect of the present invention, a dispersion of nanoparticles includes nanoparticles which have been surface-modified by adsorbing thereon the graft copolymer according to any one of the fifth to eighth aspects.

In an eleventh aspect of the present invention, a method for producing nanoparticles uses hydrophobic cores of micelles formed from the graft copolymer according to any one of the fifth to eighth aspects as a reaction field.

In a twelfth aspect of the present invention, a surface modifier includes a graft copolymer of a polymerizable monomer (A2) having a group represented by general formula (VI) and a polymerizable monomer (B2) having a repeating structure represented by general formula (VII).

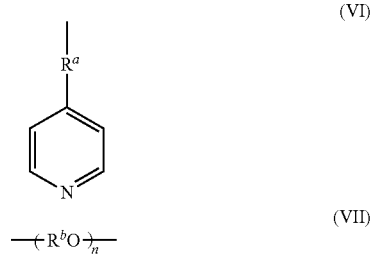

(In the formula, $R^a$ represents an alkylene group having a carbon number of 2-7, $R^b$ represents an alkylene group having a carbon number of 2-5, and n represents any integer from 5 to 2,000.)

According to a thirteenth aspect of the present invention, in the surface modifier according to the twelfth aspect, the polymerizable monomer (A2) is represented by general formula (VIII).

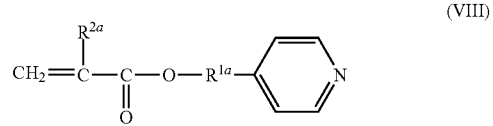

(In the formula, $R^{1a}$ represents an alkylene group having a carbon number of 2-7, and $R^{2a}$ represents a hydrogen atom or a methyl group.)

According to a fourteenth aspect of the present invention, in the surface modifier according to the twelfth or thirteenth aspect, the polymerizable monomer (B2) is represented by general formula (IX).

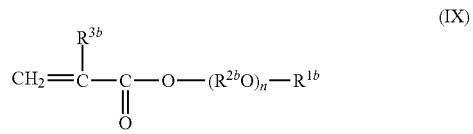

(In the formula, $R^{1b}$ represents a hydrogen atom or an alkyl group having a carbon number of 1-10, $R^{2b}$ represents an alkylene group having a carbon number of 2-5, $R^{3b}$ represents a hydrogen atom or a methyl group, and n represents any integer from 5 to 2,000.)

According to a fifteenth aspect of the present invention, in the surface modifier according to any one of the twelfth to fourteenth aspects, the polymerizable monomer (B2) has a weight-average molecular weight from 200 to 80,000.

According to a sixteenth aspect of the present invention, in the surface modifier according to any one of the twelfth to fifteenth aspects, the mole ratio of the polymerizable monomer (A2) to the polymerizable monomer (B2) is from 1:99 to 99:1.

In a seventeenth aspect of the present invention, a modified object includes an object which has been modified by adsorbing onto a surface thereof the surface modifier according to any one of the twelfth to sixteenth aspects.

In an eighteenth aspect of the present invention, a dispersion of nanoparticles includes nanoparticles which have been surface-modified by adsorbing thereon the surface modifier according to any one of the twelfth to sixteenth aspects is provided.

In a nineteenth aspect of the present invention, a method for producing nanoparticles uses hydrophobic cores of micelles formed from the surface modifier according to any one of the twelfth to sixteenth aspects as a reaction field.

Effects of the Invention

The polymerizable monomer of the present invention has a polymerizable group at one terminus and a functional group such as azide group capable of introducing a ligand at another terminus. Therefore, a graft copolymer capable of multipoint-coordinating on a surface of a material as an object to be modified, and functionalizing the surface can be obtained by synthesizing a graft copolymer between the polymerizable monomer and a polymerizable monomer having a pyridyl group.

Furthermore, the surface modifier of the present invention includes the polymerizable monomer (A2) having a group represented by general formula (VI), and thus can adsorb onto an object to be modified via a pyridyl group. The pyridyl group exhibits affinity to various modified objects, thus resulting in a surface modifier with general versatility. Furthermore, in the surface modifier of the present invention, since $R^a$ of general formula (VI) is an alkylene group having a carbon number of 2-7, particles having a small and stable particle size can be obtained. In addition, since the polymerizable monomer (B2) having a repeating structure represented by general formula (VII) is included, the object which has been modified can be stably dispersed in a solvent.

In addition, since the method for producing nanoparticles of the present invention uses hydrophobic cores of the micelles formed from the surface modifier of the present invention as a reaction field, particles having a small and stable particle size can be obtained without aggregating.

PREFERRED MODE FOR CARRYING OUT THE INVENTION

Figure 1:
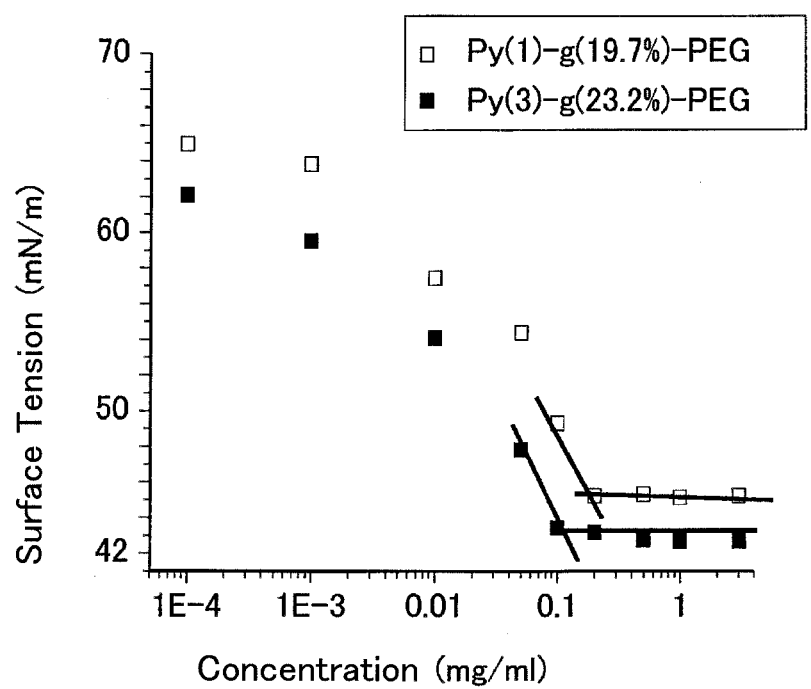
FIG. 1 is a graph showing surface tension of polymer micelles formed using a surface modifier of the present invention (m=1 and m=3)

Specific embodiments of the present invention are explained in detail below.

[Surface Modifier]

The surface modifier of the present invention consists of the graft copolymer between the polymerizable monomer (A2) having a group represented by general formula (VI) and the polymerizable monomer (B2) having a repeating structure represented by general formula (VII).

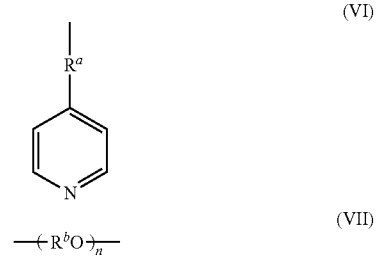

[Polymerizable Monomer (A2)]

The polymerizable monomer (A2) is a polymerizable monomer having a group represented by general formula (VI) described above. $R^a$ is characterized by being an alkylene group having a carbon number of 2-7 and preferably an alkylene group having a carbon number of 3-5. In the surface modifier of the present invention, inter-nanoparticles hydrophobic cohesion as an object to be modified can be controlled by changing the carbon number of the alkylene group. An alkylene group having a carbon number within the range described above can result in particles with a small and stable particle size.

The polymerizable monomer (A2) is a monomer capable of polymerizing and thus requires a polymerizable group in its structure; and the polymerizable group, which is not particularly limited, may be exemplified by a vinyl group, an allyl group, a styryl group, a methacryloyl group, an acryloyl group, etc. It can polymerize with the polymerizable monomer (B2) described later via the polymerizable group.

The polymerizable monomer (A2) in the surface modifier of the present invention is preferably represented by general formula (VIII).

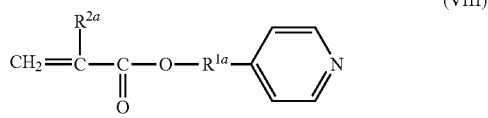

Here, $R^{1a}$ is an alkylene group having a carbon number of 2-7 and preferably an alkylene group having a carbon number of 3-5. $R^{2a}$ is a hydrogen atom or a methyl group.

[Polymerizable Monomer (B2)]

The polymerizable monomer (B2) is a polymerizable monomer having a repeating structure represented by general formula (VII). $R^b$ is characterized by being an alkylene group having a carbon number of 2-5 and preferably having a carbon number of 2 or 3. An alkylene group having a carbon number within the range described above can result in higher hydrophilicity and flexibility of the molecule. Additionally, n is characterized by being any integer from 5 to 2,000 and preferably from 10 to 500. n within the range described above can result in higher hydrophilicity and flexibility. The unit of the repeating structure represented by general formula (VII), which is not particularly limited, is exemplified by ethylene oxide, propylene oxide, etc.

The polymerizable monomer (B2) is a monomer capable of polymerizing and thus requires a polymerizable group in its structure; and the functional group, which is not particularly limited, may be exemplified by a vinyl group, an allyl group, a styryl group, a methacryloyl group, an acryloyl group, etc. It can polymerize with the polymerizable monomer (A2) described above via the polymerizable group.

The polymerizable monomer (B2) in the surface modifier of the present invention is preferably represented by general formula (IX).

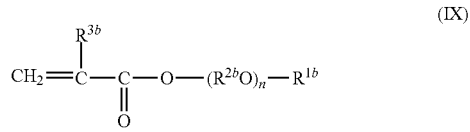

Here, $R^{1b}$ is a hydrogen atom or an alkyl group having a carbon number of 1-10 and preferably an alkyl group having a carbon number of 2-5. $R^{2b}$ is an alkylene group having a carbon number of 2-5, and $R^{3b}$ is a hydrogen atom or a methyl group. Additionally, n is characterized by being any integer from 5 to 2,000 and preferably from 10 to 500.

[Method of Synthesizing Graft Copolymer]

The surface modifier of the present invention consists of the graft copolymer between the polymerizable monomer (A2) and the polymerizable monomer (B2). In the surface modifier of the present invention, the polymerization initiator used for the graft copolymerization between the polymerizable monomer (A2) and the polymerizable monomer (B2), which is not particularly limited, is exemplified by azo-type polymerization initiators such as 2,2'-azobisisobutyronitrile (AIBN) and 2,2'-azobis(2-methylbutyronitrile), sulfate salt polymerization initiators such as ammonium persulfate and potassium persulfate, and organic peroxide polymerization initiators such as benzoyl peroxide and lauroyl peroxide.

A preferable used amount of the polymerization initiator is from 0.1% to 10% by mass based on the total amount of the polymerizable monomer (A2) and the polymerizable monomer (B2). A chain transfer agent such as mercaptoacetic acid, mercaptopropionic acid, 2-propanethiol, and 1-butanethiol may also be added to adjust the molecular weight of the graft copolymer.

Polymerization time, which depends on temperature and properties of a desired final product, is from 1 to 48 hours, preferably at from 30° C. to 90° C. and more preferably at from 50° C. to 70° C.

In the surface modifier of the present invention, the weight-average molecular weight (measured by GPC) of the graft copolymer is preferably from 1,000 to 500,000, and more preferably from 2,000 to 100,000. Here, by adjustment within this range, the object to be modified may be imparted with interfacial stability.

In the surface modifier of the present invention, the weight-average molecular weight (measured by GPC) of the polymerizable monomer (B2) is preferably from 200 to 80,000, and more preferably from 500 to 20,000. Dispersion stability of the nanoparticles in a solvent can be controlled by changing the molecular weight of the polymerizable monomer (B2). Here, by adjustment within this range, the nanoparticles can be stably dispersed in a solvent.

In the surface modifier of the present invention, the mole ratio of (polymerizable monomer (A2))/(polymerizable monomer (B2)) is preferably from 1:99 to 99:1, and more preferably from 10:90 to 90:10. Hydrophile-lipophile balance can be controlled by changing the mole ratio of the polymerizable monomer (A2) to the polymerizable monomer (B2). Here, by adjustment within this range, the surface modifier of the present invention can be stably adsorbed onto the surface of an object to be modified and the object which has been modified on the surface (hereinafter, may be referred to as "modified object") can be stably dispersed in a solvent.

[Modified Object]

In the modified object of the present invention, the object has been modified by adsorbing the surface modifier of the present invention onto the surface thereof. The surface modifier of the present invention functions due to the pyridyl group, which is a basic functional group, adsorbing onto the surface of the object to be modified. It is therefore preferred that the modified object of the present invention provides an acidic surface onto which the pyridyl group, which is a basic functional group, can easily adsorb. The type or configuration thereof is not limited as long as the surface is acidic. It is exemplified by metal oxides such as silica and alumina; metal salts such as sodium carbonate, sodium hydrogen carbonate, and aluminum hydroxide; carbon materials such as carbon black, mesoporous carbon, fullerene, carbon nanotube, and graphite; inorganic fiber materials such as glass fiber and carbon fiber; metals such as gold, silver, iron, and copper; metalloid oxides, semiconductors, etc.

The modified object of the present invention is produced by performing the modification to allow the surface modifier of the present invention to adsorb onto the surface; therefore, the modified object can suppress adsorption of protein etc. when it is applied to medical apparatuses etc. used in living bodies, for example.

In the modified object of the present invention, the surface thereof may be partially or entirely coated with the surface modifier. The coating process, which is not particularly limited, is exemplified by adsorption processes, dip coating processes, etc.

[Dispersion of Nanoparticles]

The dispersion of the present invention is a solution in which nanoparticles surface-modified with the surface modifier of the present invention are dispersed. The types of nanoparticles dispersed in the dispersion of the present invention, which are not particularly limited, are exemplified by carbon materials such as carbon black, mesoporous carbon, fullerene, carbon nanotube, and graphite; metals such as gold, silver, iron, and copper; semiconductors; inorganic oxides; etc. Transition metals such as copper, silver, gold, nickel, palladium, platinum, and cobalt are preferable in a case of metal. One or two or more types of metal may be used. Gold, silver, and platinum are more preferable in view of ease of reduction and ease of handling.

The content of nanoparticles in the dispersion of the present invention is not particularly limited, but a lower content may decrease availability thereof and a higher content may degrade flowability, which is preferably taken into account in order to appropriately arrange the content depending on the purpose.

The particle size of nanoparticles, which is not particularly limited, is preferably from 2 to 200 nm, and more preferably from 10 to 100 nm for the purpose of higher dispersion stability. In the dispersion of the present invention, the solvent is not particularly limited and may be water or an organic solvent. Additionally, the nanoparticles dispersed in the dispersion of the present invention are surface-modified with the surface modifier of the present invention; therefore the nanoparticles can stably disperse even under easily-oxidizable conditions or high ionic strength conditions, for example.

[Method for Producing Nanoparticles]

The method for producing nanoparticles of the present invention uses hydrophobic cores of the micelles formed from the surface modifier as a reaction field. In a case of metal nanoparticles, for example, the nanoparticles can be produced by adding an ion solution of a metal salt or a metal to a solvent which disperses the surface modifier of the present invention, and reducing the metal ion.

In the method for producing nanoparticles of the present invention, the solvent, which is not particularly limited, is preferably water, methanol, ethanol, 2-propanol, DMSO, toluene, or the like from the viewpoint of mild reducing ability.

[Polymerizable Monomer (A1)]

The polymerizable monomer (A1) is represented by general formula (III).

$$R^{1a}+R^{2a}O)_{n}R^{3a} \tag{III}$$

In general formula (III), $R^{1a}$ represents a polymerizable group. The polymerizable group, which is not particularly limited, is exemplified by the groups represented by general formula (IV), a vinyl group, an allyl group, a styryl group, a vinyl phenyl alkoxy group, etc.

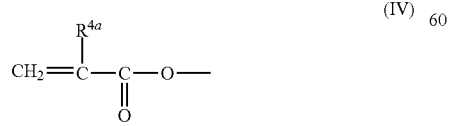

(In the formula, $R^{4a}$ represents a hydrogen atom or an alkyl group having a carbon number of 1-10.)

Among these, the groups represented by general formula (IV) are preferable, and a (meth)acryloyl group where $R^{4a}$ is a hydrogen atom or a methyl group is more preferable. The polymerizable monomer (A1) can copolymerize with other polymerizable monomers via the polymerizable group.

$R^{2a}$ represents an alkylene group having a carbon number of 2-5 and is preferably an ethylene group or a propylene group.

Here, n represents any integer from 5 to 2,000 and is preferably from 10 to 500. When nanoparticles are used as an object to be modified, dispersion stability of the nanoparticles in a solvent can be controlled by changing the value of n.

$R^{3a}$ represents an organic group having at the terminus a functional group selected from among an azide group, a phenyl azide group, a carboxyl group, a primary to quaternary amino group, an acetal group, an aldehyde group, a thiol group, a disulfide group, an active ester group, a trialkoxysilyl group, and a polymerizable group. The organic group, which is not particularly limited as long as it has a functional group such as an azide group, is exemplified by alkyl groups having an azide group etc. at the terminus. The polymerizable monomer (A1) can be introduced with a ligand via the functional group at the terminus.

In the polymerizable monomer (A1) of the present invention, the weight-average molecular weight (measured by GPC) is preferably from 200 to 80,000, and more preferably from 500 to 20,000. Even when the nanoparticles are used as the object to be modified, the nanoparticles can be dispersed more stably in a solvent by adjusting the weight-average molecular weight of the polymerizable monomer (A1) within the range described above.

[Method for Synthesizing Polymerizable Monomer (A1)]

Among the polymerizable monomers (A1) of the present invention represented by general formula (III), the polymerizable monomer (A1), in which $R^{1a}$ is a group expressed by general formula (IV), $R^{2a}$ is an ethylene group, and $R^{3a}$ is an alkyl group having an azide group at the terminus, can be produced by the steps from (a) to (e) below in sequence, for example.

(a) Initially a hydroxyl group at one terminus of ethylene glycol represented by formula (1) is protected with a tetrahydropyranyl group (THP group) to prepare the compound represented by formula (2).

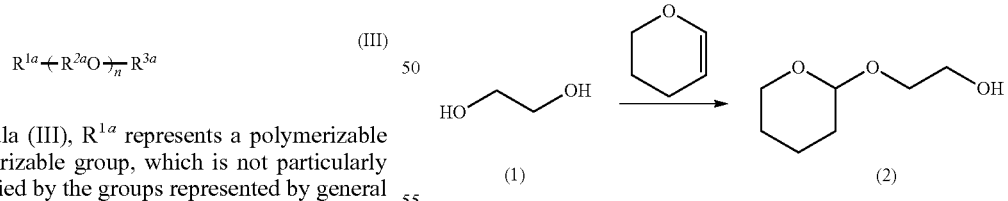

(1)                                                    (2)

(b) Next, the compound represented by formula (2) and ethylene oxide are reacted to prepare the compound represented by formula (3).

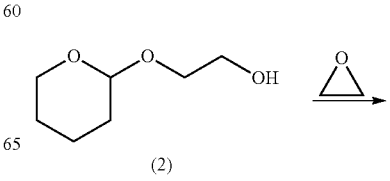

(2)

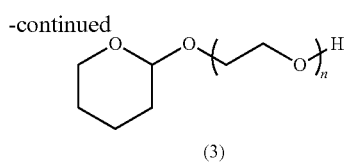

(3)

(In the formula, n represents any integer from 5 to 2,000.)

(c) Next, the compound represented by formula (3) and the compound represented by formula (4) are reacted to prepare the compound represented by formula (5).

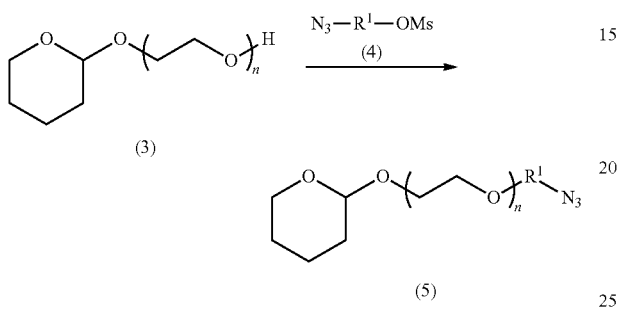

(In the formula, $R^1$ represents an alkylene group having a carbon number of 1-10, and Ms represents a mesyl group.)

(d) Next, the tetrahydropyranyl group of the compound represented by formula (5) is deprotected to prepare the compound represented by formula (6).

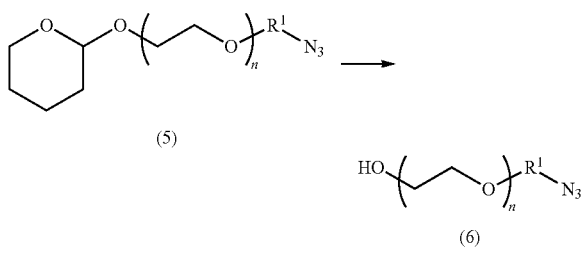

(e) Finally, the compound represented by formula (6) and the compound represented by formula (7) are reacted to prepare the compound represented by formula (8).

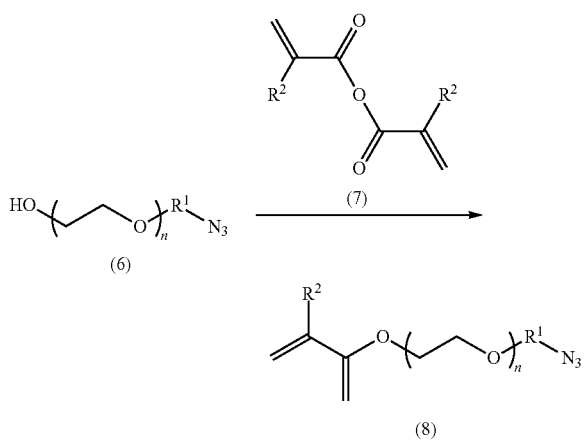

(In the formula, $R^2$ is an alkyl group having a carbon number of 1-10.)

[Graft Copolymer]

The graft copolymer of the present invention is one prepared by graft-copolymerizing the polymerizable monomer (A1) represented by general formula (III) and the polymerizable monomer having a pyridyl group (B1). Explanation in regards to the polymerizable monomer (A1) is omitted.

[Polymerizable Monomer (B1)]

The polymerizable monomer (B1) has a polymerizable group. The polymerizable group, which is not particularly limited, is exemplified by groups similar to those of the polymerizable monomer (A1).

The polymerizable monomer (B1) is preferably represented by general formula (V).

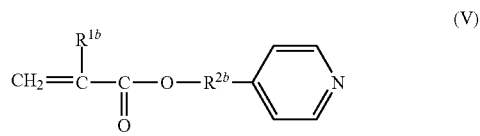

Here, $R^{1b}$ is a hydrogen atom or an alkyl group having a carbon number of 1-10 and preferably a hydrogen atom or a methyl group. $R^{2b}$ is an alkylene group having a carbon number of 1-7, preferably an alkylene group having a carbon number of 2-7, and more preferably an alkylene group having a carbon number of 3-5.

[Method for Synthesizing Graft Copolymer]

The graft copolymer of the present invention consists of the polymerizable monomer (A1) and the polymerizable monomer (B1). The polymerization initiator, used for the graft copolymerization between the polymerizable monomer (A1) and the polymerizable monomer (B1), is not particularly limited and is exemplified by azo-type polymerization initiators such as 2,2'-azobisisobutyronitrile (AIBN) and 2,2'-azobis(2-methylbutyronitrile), sulfate salt polymerization initiators such as ammonium persulfate and potassium persulfate, and organic peroxide polymerization initiators such as benzoyl peroxide and lauroyl peroxide.

A preferable used amount of the polymerization initiator is from 0.1% to 10% by mass based on the total amount of the polymerizable monomer (A1) and the polymerizable monomer (B1). A chain transfer agent such as mercaptoacetic acid, mercaptopropionic acid, 2-propanethiol, and 1-butanethiol may also be added to adjust the molecular weight of the graft copolymer.

Polymerization time, which depends on temperature and properties of a desired final product, is from 1 to 48 hours, preferably at from 30° C. to 90° C. and more preferably at from 50° C. to 70° C.

The weight-average molecular weight (measured by GPC) of the graft copolymer is preferably from 1,000 to 500,000, and more preferably from 2,000 to 100,000. Here, by adjustment within this range, the object to be modified may be imparted with interfacial stability.

In the graft copolymer of the present invention, the mole ratio of (polymerizable monomer (A1))/(polymerizable monomer (B1)) is preferably from 1:99 to 99:1, and more preferably from 10:90 to 90:10. Hydrophile-lipophile balance can be controlled by changing the mole ratio of the polymerizable monomer (A1) to the polymerizable monomer (B1). Here, by adjustment within this range, stable adsorption onto the surface of an object to be modified can be achieved, and the surface-modified object can be stably dispersed in a solvent.

[Functionalization of Graft Copolymer]

The graft copolymer of the present invention can be bonded with a ligand via a functional group at the terminus of $R^{3a}$ in general formula (III). The ligand is exemplified by various sugars (sugar chain), antibodies, peptides, oligo DNAs, etc. Various functions can be added to the graft copolymer by bonding the ligand thereto.

The functionalization may be carried out by reacting the functional group at the terminus of $R^{3a}$ in general formula (III) and the ligand or by introducing another functional group to the ligand and then reacting it with the functional group at the terminus. For example, when the ligand is lactose, an alkyl group is previously introduced to the lactose and then reacted with the functional group at the terminus of the graft copolymer.

[Surface Modification Using Functionalized Graft Copolymer]

In the graft copolymer of the present invention, the pyridyl group, which is a basic functional group, adsorbs onto the surface of a material as an object to be modified by multipoint coordination. It can stably adsorb onto the object to be modified by virtue of the multipoint coordination. It is preferred that the object to be modified has an acidic surface onto which the pyridyl group, which is a basic functional group, can easily adsorb. The type or configuration thereof is not limited as long as it is an acidic surface.

The object to be modified is exemplified by sensors, diagnosis particles, separating substrates for biological molecules, cell culture substrates, etc.

Type thereof are exemplified by metal oxides such as silica and alumina; metal salts such as sodium carbonate, sodium hydrogen carbonate, and aluminum hydroxide; carbon materials such as carbon black, mesoporous carbon, fullerene, carbon nanotube, and graphite; inorganic fiber materials such as glass fiber and carbon fiber; metals such as gold, silver, iron, and copper; metalloid oxides, semiconductors, etc. Here, transition metals such as copper, silver, gold, nickel, palladium, platinum, and cobalt are preferable in a case of metal. One or two or more types of metal may be used. Gold, silver, and platinum are more preferable in view of ease of reduction and ease of handling.

The configuration thereof is exemplified by substrates, nanoparticles, etc. In the case of nanoparticles, the object to be modified can be stably dispersed in a solvent. Here, the solvent may be water or an organic solvent under easily-oxidizable conditions or high ionic strength conditions.

The process for adsorbing the graft copolymer of the present invention onto the surface of a material of an object to be modified is not particularly limited and is exemplified by adsorption processes, dip coating processes, etc.

The graft copolymer of the present invention can stably adsorb onto the object to be modified as described above. Accordingly, the graft copolymer, which can modify nanoparticles as the object to be modified and is bonded with sugar chains or antibodies having a function to recognize a target cell or tissue of an infection or cancer as the ligand, can be favorably utilized for diagnostic cell/tissue sensing probes, active targeting drug delivery systems (active target oriented DDS), for example.

EXAMPLES

The present invention is explained more specifically with reference to examples below; however, the present invention is not limited to the examples.

[Synthesis of Graft Copolymer]

A polymerizable monomer (A2) and a polymerizable monomer (B2) were copolymerized to synthesize a graft copolymer (Py-g-PEG) as shown in the reaction scheme below.

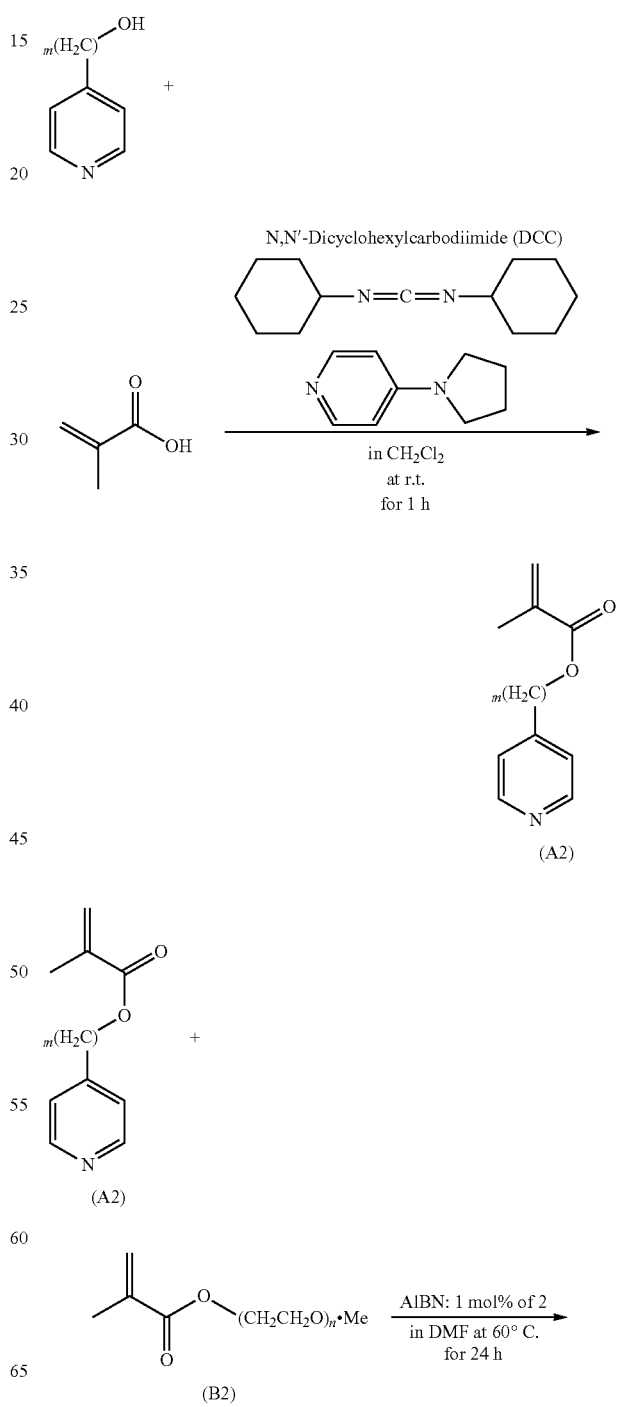

-continued

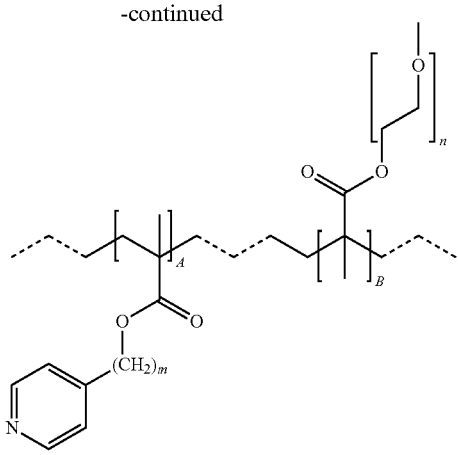

Synthesis of Polymerizable Monomer (A2)

Synthesis Example 1

Case of Alkylene Group Having a Carbon Number of 1: m=1

After 5.45 g (50 mmol) of 4-pyridinemethanol (manufactured by Aldrich Co.), 4.73 g (55 mmol) of methacrylic acid (manufactured by Aldrich Co.), and 740 mg (5 mmol) of 4-(1-pyrrolidinyl)pyridine (manufactured by Aldrich Co.) were dissolved in 100 ml of anhydrous dichloromethane (manufactured by WAKO Co.), 11.3 g (55 mmol) of N,N'-dicyclohexylcarbodiimide (DCC) (manufactured by Aldrich Co.) was added thereto and allowed to react at room temperature for 1 hour. Then, insoluble urea was removed by filtration, followed by removal of solvent under reduced pressure. The residual material was purified by column chromatography (column: silica (manufactured by WAKO Co.), solvent: hexane/ethyl acetate) to obtain 8.1 g (46 mmol) of a colorless oil (yield rate: 91%).

Synthesis Example 2

Case of Alkylene Group Having a Carbon Number of 3: m=3

After 6.85 g (50 mmol) of 4-pyridinepropanol (manufactured by Aldrich Co.), 4.73 g (55 mmol) of methacrylic acid, and 740 mg (5 mmol) of 4-(1-pyrrolidinyl)pyridine were dissolved in 100 ml of anhydrous dichloromethane, 11.3 g (55 mmol) of DCC was added thereto and allowed to react at room temperature for 1 hour. Then, insoluble urea was removed by filtration, followed by removal of solvent under reduced pressure. The residual material was purified by column chromatography (column: silica (manufactured by WAKO Co.), solvent: hexane/ethyl acetate) to obtain 8.5124 g (41.4 mmol) of a colorless oil (yield rate: 82.8%).

Synthesis Example 3

Case of Alkylene Group Having a Carbon Number of 5: m=5

9-Borabicyclo[3.3.1]nonane (9-BBN) dissolved in 15 ml of tetrahydrofuran (manufactured by Aldrich Co.) was added to 300 mg (3.483 mmol) of 4-pentene-1-ol and allowed to react at 25° C. for 24 hours. Then, 4-bromopyridine hydrochloride (manufactured by Aldrich Co.) dissolved in water/dimethylformamide (DMF) at a ratio of 2:8, tetrakis(triphenylphosphine)palladium (manufactured by Aldrich Co.), and potassium carbonate (manufactured by Aldrich Co.) were added thereto in an equivalent ratio of 1:1.2:0.2 and allowed to react at 70° C. for 6 hours. Then, solvent was removed under reduced pressure, and the residual material was diluted with ethyl acetate and filtered with Celite. The material thus obtained was purified by column chromatography (column: silica (manufactured by Aldrich Co.), solvent: ethyl acetate/hexane) to obtain 203 mg of pyridinepentanol (yield rate: 48%). The reaction scheme is shown below.

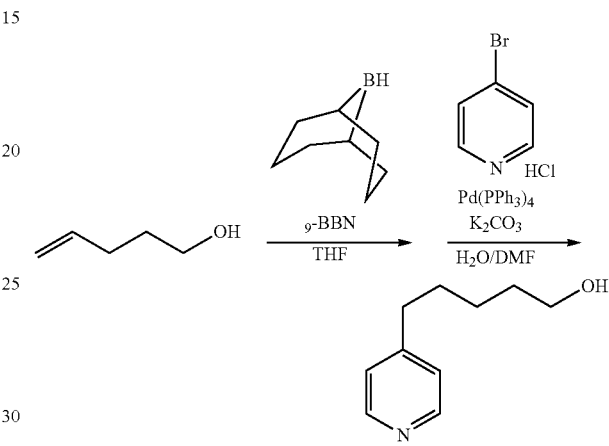

After 110 mg (0.666 mmol) of the pyridinepentanol resulting from the reaction described above, methacrylic acid (3 equivalents of pyridinepentanol), and triethylamine (3 equivalents of pyridinepentanol) were dissolved in 9 ml of anhydrous dichloromethane, DCC (3 equivalents of pyridinepentanol) was added thereto and allowed to react at room temperature for 1 hour. Then, insoluble urea was removed by filtration, followed by removal of solvent under reduced pressure. The residual material was purified by column chromatography (column: silica (manufactured by Aldrich Co.), solvent: hexane/ethyl acetate) to obtain 64 mg of a colorless oil (yield rate: 31%).

Synthesis of Graft Copolymer

Synthesis Example 4

Case of Polymerizable Monomer (A2) Resulting from Synthesis Example 1

After 177 mg (1.0 mmol) of 1,4-pyridinemethanol-methacrylate resulting from Synthesis Example 1, 624 mg (0.3 mmol) of α-methyl-ω-methacryloyl-polyethylene glycol (manufactured by Aldrich Co.), and 2,2'-azobisisobutyronitrile (AIBN) (manufactured by WAKO Co.) in 1% by mass of 1,4-pyridinemethanol-methacrylate were dissolved in 8 ml of DMF, the solution was subjected to 3 cycles of freeze-degassing, followed by allowing to react at 60° C. for 24 hours. The reaction liquid was added dropwise into a repreipitation solvent (isopropyl alcohol (manufactured by WAKO Co.)/diethyl ether (manufactured by Aldrich Co.)=1/20 in volume ratio) in 20 times amount of DMF and stirred for several minutes. Then, 401 mg (5.1 μmol) of a white powder was obtained through centrifugal separation and freeze dehydration (yield rate: 50%).

Synthesis Example 5

Case of Polymerizable Monomer (A2) Resulting from Synthesis Example 2

After 205 mg (10 mmol) of 4-pyridinepropanol-methacrylate resulting from Synthesis Example 2, 208 mg, 624 mg, or 1248 mg (0.1 mmol, 0.3 mmol, or 0.6 mmol) of α-methyl-ω-methacryloyl-polyethylene glycol, and AIBN as 1% by mass of 4-pyridinepropanol-methacrylate were dissolved in DMF (4 ml, 8 ml, or 14 ml), the solution was subjected to 3 cycles of freeze-degassing, followed by allowing to react at 60° C. for 24 hours. The reaction liquid was added dropwise into a reprecipitation solvent (isopropyl alcohol (manufactured by WAKO Co.)/diethyl ether (manufactured by Aldrich Co.)=1/20 in volume ratio) in 20 times amount of DMF and stirred for several minutes. Then, 202 mg, 489 mg, or 828 mg (1.8 μmol, 4.1 μmol, or 12.8 μmol) of a white powder was obtained through centrifugal separation and freeze dehydration (yield rate: 49%, 59%, or 57%).

Synthesis Example 6

Case of Polymerizable Monomer (A2) Resulting from Synthesis Example 3

After 205 mg (10 mmol) of 4-pyridinepentanol-methacrylate resulting from Synthesis Example 3, 208 mg, 624 mg, or 1248 mg (0.1 mmol, 0.3 mmol, or 0.6 mmol) of α-methyl-ω-methacryloyl-polyethylene glycol, and AIBN as 1% by mass of 4-pyridinepentanol-methacrylate were dissolved in DMF (4 ml, 8 ml, or 14 ml), the solution was subjected to 3 cycles of freeze-degassing, followed by allowing to react at 60° C. for 24 hours. The reaction liquid was added dropwise into a reprecipitation solvent (isopropyl alcohol (manufactured by WAKO Co.)/diethyl ether (manufactured by Aldrich Co.)=1/20 in volume ratio) in 20 times amount of DMF and stirred for several minutes. Then, 220 mg, 411 mg, or 928 mg of a white powder was obtained through centrifugal separation and freeze dehydration (yield rate: 52%, 41%, or 55%).

Synthesis of Comparative Product

Synthesis Example 7

Case of Polyethylene Glycol Having Pyridyl Group at Chain Terminus (Py-PEG-MeO)

After 1.14 g (0.50 mmol) of α-methyl-ω-methyl(4-pyridylmethyl carboxylate)polyethylene glycol, 109 mg (1.0 mmol) of 4-pyridinemethanol, and 15 mg (0.10 mmol) of 4-(1-pyrrolidinyl)pyridine were dissolved in 20 ml of anhydrous dichloromethane, 113 mg (0.55 mmol) of DCC was added thereto and allowed to react at room temperature for 1 hour. Then, insoluble urea was removed by filtration, followed by removal of solvent under reduced pressure. 2-Propanol of 5 ml was added dropwise into the residual material and stirred for several minutes. After centrifugal separation of a precipitate, 697 mg (0.3 mmol) of a white powder was obtained through freeze dehydration (yield rate: 68%).

Table 1 shows types of synthesized graft copolymers (Py-g-PEG), carbon number (m) of alkylene group in $R^a$ of polymerizable monomer (A2) represented by general formula repeat number (n) of ethylene oxide unit, number-average molecular weight (Mn) of Py-g-PEG, dispersion degree (Mw/Mn) of Py-g-PEG, and copolymerization ratio (PEG/Py) of polyethylene glycol (PEG) to pyridine (Py). Here, the molecular weight was measured by gel permeation chromatography (GPC).

TABLE 1

| | m | n | Mn | Mw/Mn | PEG/Py (%) |
|---|---|---|---|---|---|
| Py(1)-g(19.7%)-PEG | 1 | 43 | 67.899 | 1.545 | 19.7 |
| Py(3)-g(10.3%)-PEG | 3 | 43 | 113.180 | 1.634 | 10.3 |
| Py(3)-g(23.2%)-PEG | 3 | 43 | 119.247 | 1.557 | 23.2 |
| Py(3)-g(58.5%)-PEG | 3 | 43 | 67.498 | 1.511 | 58.5 |

[Measurement of Surface Tension]
Comparison Between m=1 and m=3

Polymer micelles were formed using Py(1)-g(19.7%)-PEG in which the carbon number (m) of alkylene group in $R^a$ of the polymerizable monomer (A2) represented by general formula (VI) is 1 and Py(3)-g(23.2%)-PEG in which the carbon number (m) is 3, and their surface tensions were measured. The micelles were formed by dissolving Py(1)-g(19.7%)-PEG or Py(3)-g(23.2%)-PEG in N,N-dimethylacetamide (DMA), introducing it into a dialysis membrane (molecular weight cut off: about 10,000), and dialyzing against water in 300 times amount of DMA for 4 days.

TABLE 2

| | m | n | $\gamma_{cmc}$ (mN/m) | cmc (mg/ml) | $A_{cmc}$ (nm²/Molecule) |
|---|---|---|---|---|---|
| Py(1)-g(19.7%)-PEG | 1 | 43 | 44.8 | 0.147 | 1.48 |
| Py(3)-g(23.2%)-PEG | 3 | 43 | 42.7 | 0.115 | 1.27 |

As shown in FIG. 1 and Table 2, m=3 exhibits lower values than those of m=1 with respect to surface tension ($\gamma_{cmc}$) as well as critical micelle concentration (cmc) and displays better surface orientation. The reason is believed that m=3 increases hydrophobic cohesion more significantly than m=1.

[Measurement of Particle Size]
Comparison Between m=1 and m=3

Figure 2A:
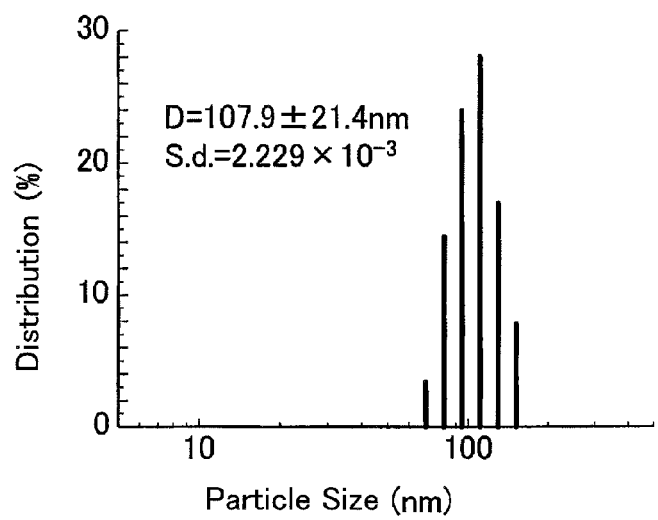
FIG. 2A is a graph showing particle size distribution of polymer micelles formed using a surface modifier of the present invention (m=1)
Figure 2B:
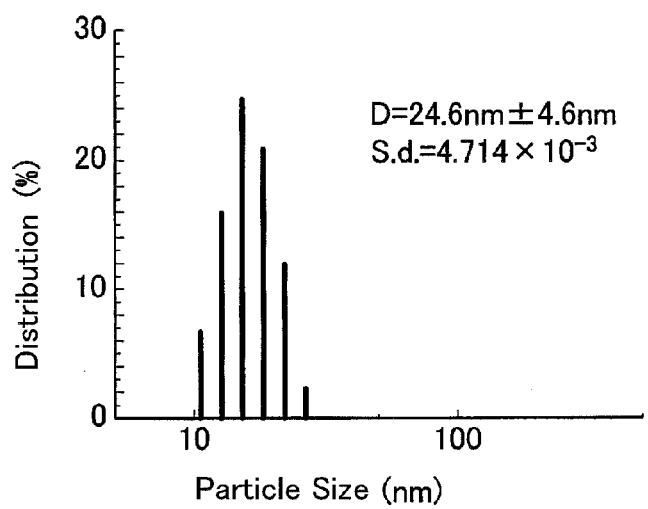
FIG. 2B is a graph showing particle size distribution of polymer micelles formed using a surface modifier of the present invention (m=3)
Figure 3A:
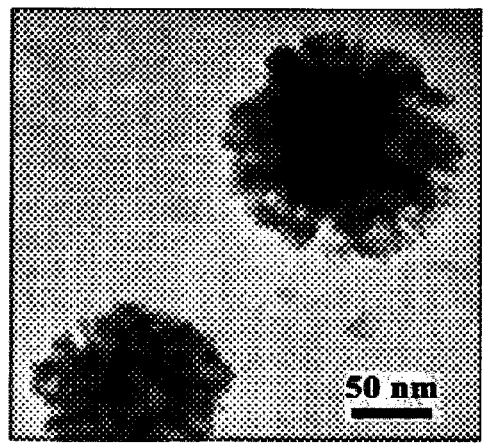
FIG. 3A is a view showing TEM images of polymer micelles formed using a surface modifier of the present invention (m=1)
Figure 3B:
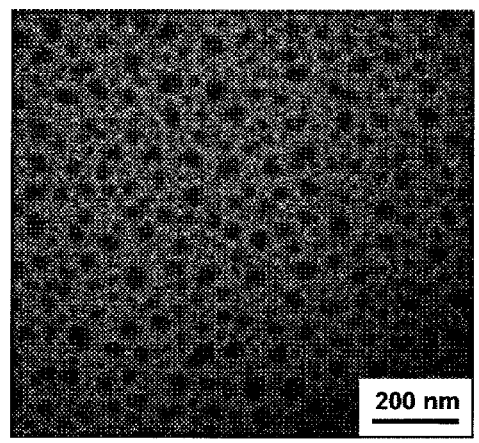
FIG. 3B is a view showing TEM images of polymer micelles formed using a surface modifier of the present invention (m=3)

Polymer micelles were formed using Py(1)-g(19.7%)-PEG or Py(3)-g(23.2%)-PEG, and the particle size was measured by a dynamic light scattering photometer (DLS) (DLS-7000, manufactured by Otsuka Electronics Co.) and a transmission electron microscope (TEM) (HITACHI H-9500, manufactured by Hitachi, Ltd.). The method for forming the micelles was similar to the method described above. The measurement results by DLS are shown in FIG. 2A (m=1), FIG. 2B (m=3) and the measurement results by TEM are shown in FIG. 3A (m=1), FIG. 3B (m=3).

As shown in FIG. 2, m=3 (average particle size: 24.6±4.6 nm) produced micelles having a smaller particle size and higher uniformity than those of m=1 (average particle size: 107.9±21.4 nm). It could also be confirmed that uniform micelles were formed in m=3 (see FIG. 3). This is believed to be due to stable cohesion in micelles since hydrophobic cohesion in m=3 increases.

[Measurement of Surface Tension]
Comparison of PEG/Py

Py(3)-g(10.3%)-PEG, Py(3)-g(23.2%)-PEG, and Py(3)-g(58.5%)-PEG were synthesized by changing a copolymerization ratio (PEG/Py) of polyethylene glycol (PEG) to pyridine (Py). Surface tensions of polymer micelles formed therefrom were measured. The method for forming the micelles was similar to the method described above. The results are shown in Table 3 and FIG. 4.

TABLE 3

|  | m | n | $\gamma_{cmc}$ (mN/m) | cmc (mg/ml) | $A_{cmc}$ (nm$^2$/Molecule) |
|---|---|---|---|---|---|
| Py(3)-g(10.3%)-PEG | 3 | 43 | 48.1 | 0.935 | 2.19 |
| Py(3)-g(23.2%)-PEG | 3 | 43 | 42.7 | 0.115 | 1.27 |
| Py(3)-g(58.5%)-PEG | 3 | 43 | 52.4 | 0.949 | 2.34 |

Figure 4:
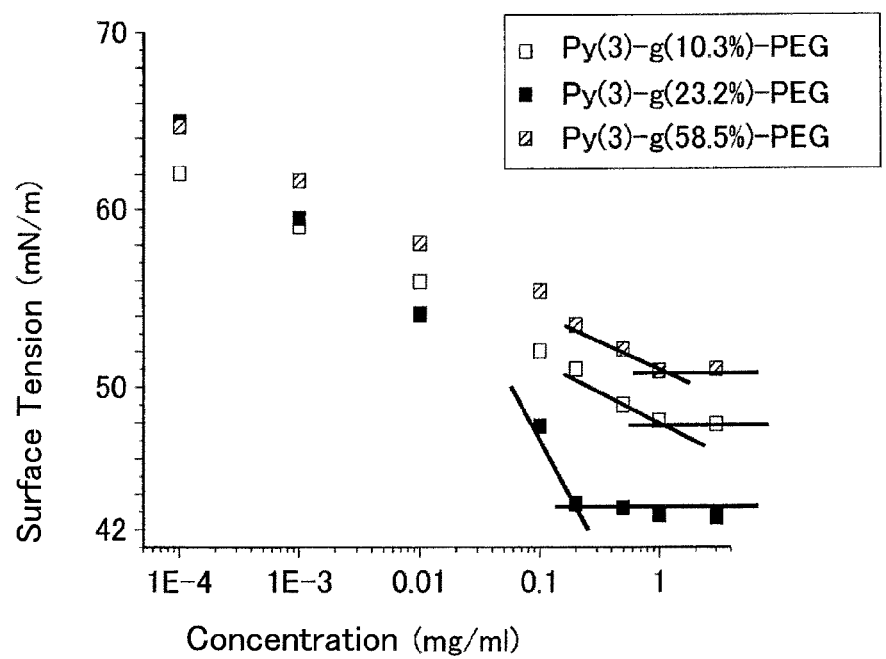
FIG. 4 is a graph showing surface tension of polymer micelles formed using a surface modifier of the present invention (m=3, (A) PEG/Py=10.3%, (B) PEG/Py=23.2%, (C) PEG/Py=58.5%)

As shown in Table 3 and FIG. 4, lowest values of surface tension ($\gamma_{cmc}$) and critical micelle concentration appeared and surface orientation was better when PEG/Py was 23.2%.

[Measurement of Particle Size]
Comparison of PEG/Py: m=3

Figure 5A:
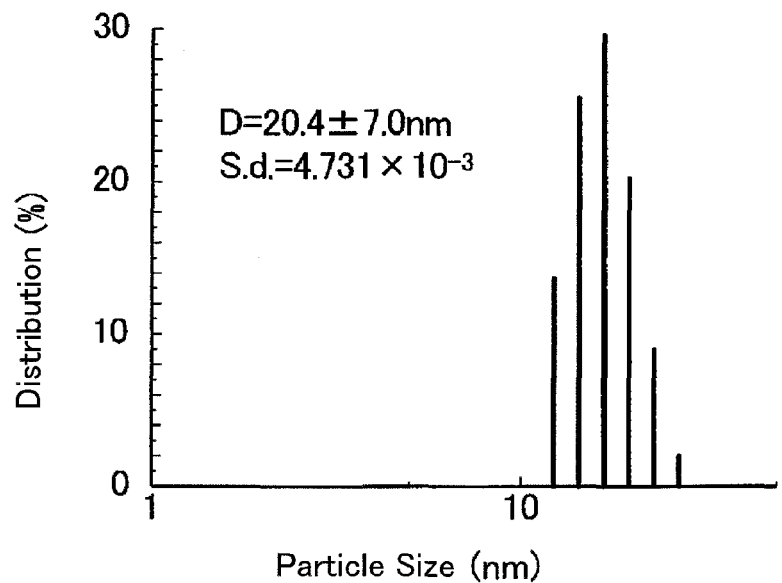
FIG. 5A is a graph showing particle size distribution of polymer micelles formed using a surface modifier of the present invention (m=3, PEG/Py=10.3%)
Figure 5B:
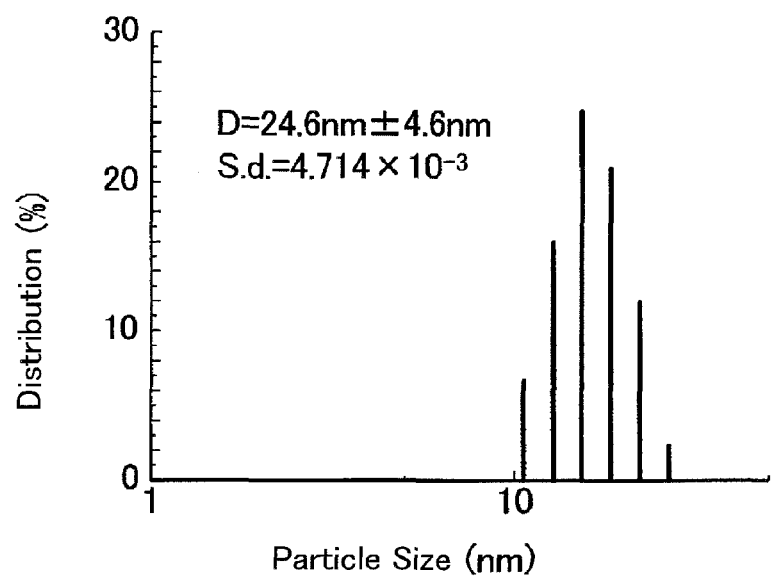
FIG. 5B is a graph showing particle size distribution of polymer micelles formed using a surface modifier of the present invention (m=3, PEG/Py=23.2%)
Figure 5C:
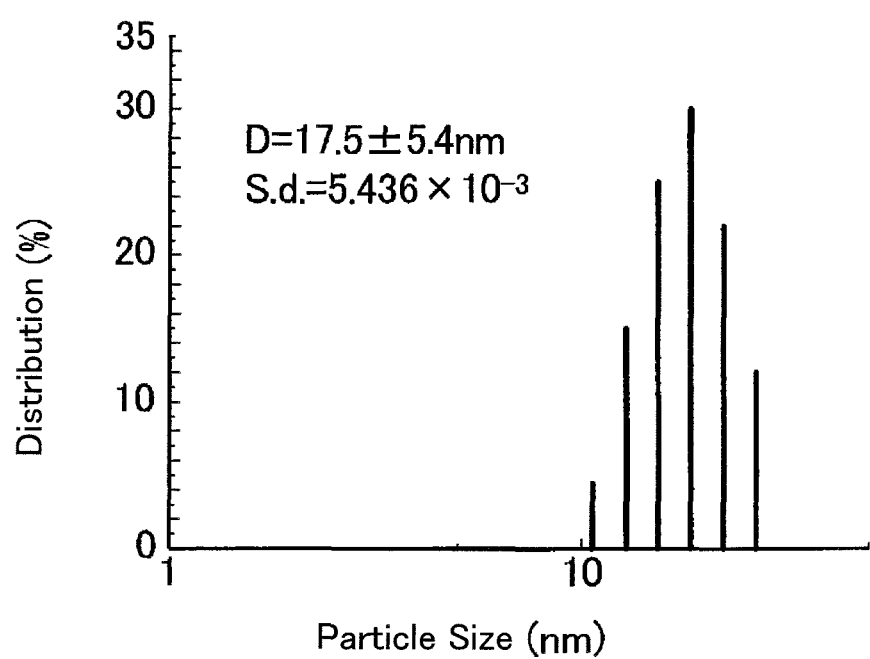
FIG. 5C is a graph showing particle size distribution of polymer micelles formed using a surface modifier of the present invention (m=3, PEG/Py=58.5%)

Polymer micelles were formed using Py(3)-g(10.3%)-PEG, Py(3)-g(23.2%)-PEG, and Py(3)-g(58.5%)-PEG, and their particle sizes were measured by DLS. The method for forming the micelles was similar to the method described above. The measurements results by DLS are shown in FIG. 5A (10.3%), FIG. 5B (23.2%), FIG. 5C (58.5%).

As shown in FIG. 5, uniform particles having a particle size of about 20 nm were formed in all micelles regardless of copolymerization ratio (PEG/Py).

[Preparation of Gold Nanoparticles]

Gold nanoparticles were prepared using hydrophobic cores of the polymer micelles formed from Py(3)-g(23.2%)-PEG as a nano-reaction field.

Chloroauric acid (manufactured by Aldrich Co.) was mixed in an amount of 0.2 mM to the polymer micelle solution (0.2 mg/ml, 3 ml) formed from Py(3)-g(23.2%)-PEG and stirred at room temperature for 24 hours. Then, 50 μl (0.1 mg/ml) of aqueous hydrazine solution (manufactured by WAKO Co.) was added thereto as a reducing agent and allowed to react.

[Measurement of Ultraviolet-Visible Absorption Spectra of Dispersion of Gold Nanoparticles]

Figure 6:
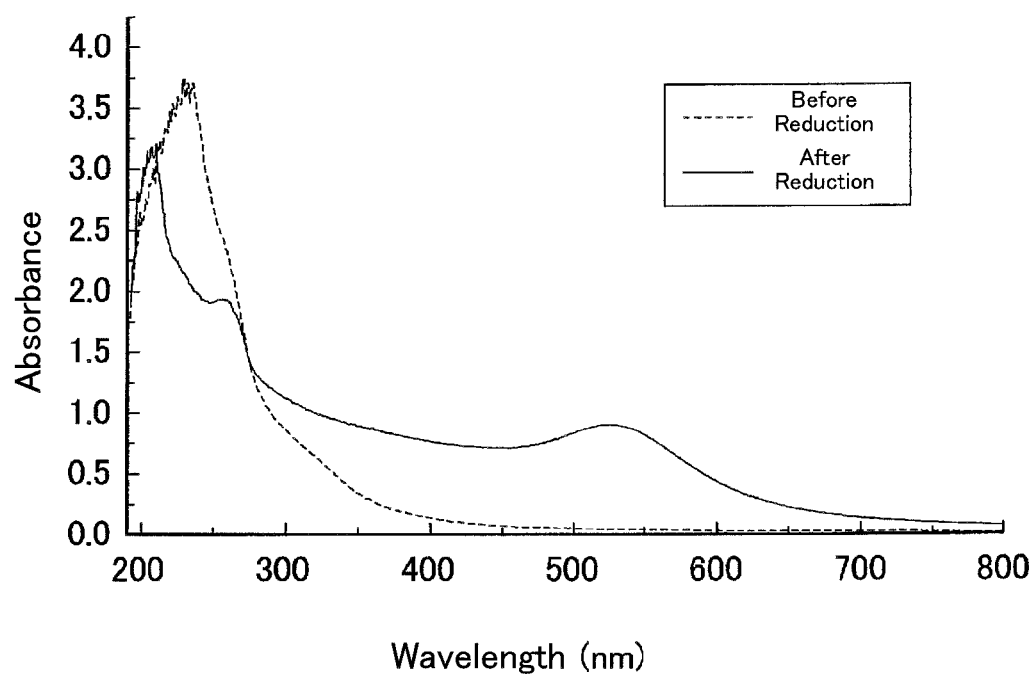
FIG. 6 is a graph showing ultraviolet-visible absorption spectra of a dispersion of gold nanoparticles of the present invention.

Ultraviolet-visible absorption spectra of the dispersion of the gold nanoparticles resulting from the method described above were measured by an ultraviolet-visible absorption spectrophotometer (Agilent 8453A Diod Array, manufactured by Agilent Co.). The results are shown in FIG. 6. As a result, a peak at 540 nm attributable to the gold nanoparticles was confirmed.

[Measurement of Particle Size of Gold Nanoparticles]

Figure 7:
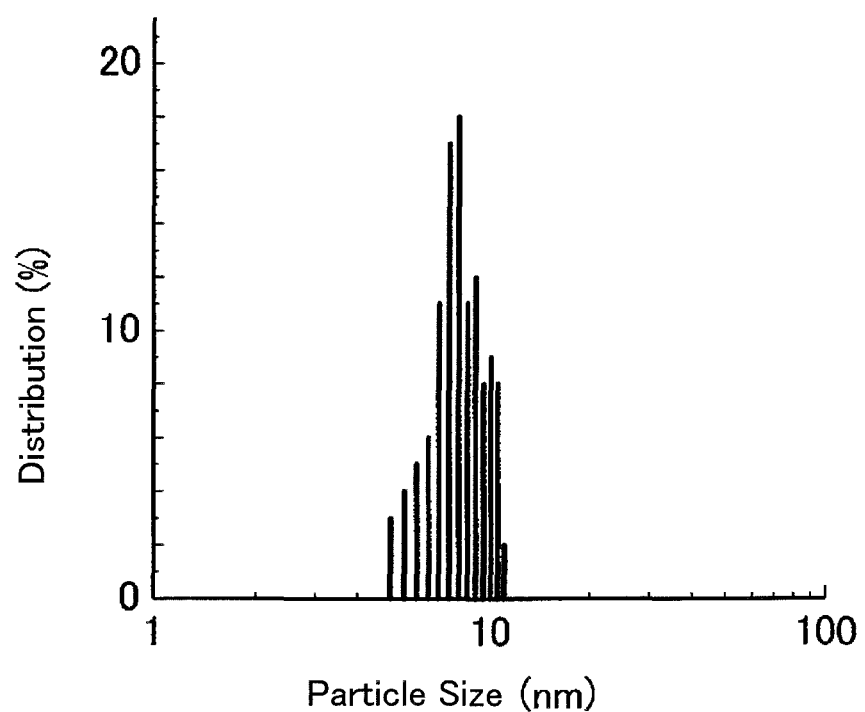
FIG. 7 is a graph showing particle size distribution of gold nanoparticles of the present invention (m=3, PEG/Py=23.2%)
Figure 8:
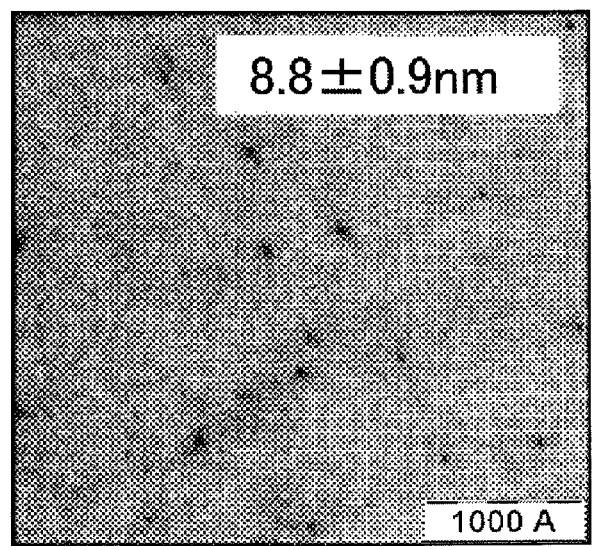
FIG. 8 is a view showing a TEM image of gold nanoparticles of the present invention (m=3, PEG/Py=23.2%)

Particle sizes of the gold nanoparticles resulting from the method described above were measured by DLS and TEM. The measurement results by DLS are shown in FIG. 7 and the measurement results by TEM are shown in FIG. 8. As a result, it was confirmed that relative monodisperse gold nanoparticles having an average particle size of 8.8±0.9 nm were generated.

Figure 9:
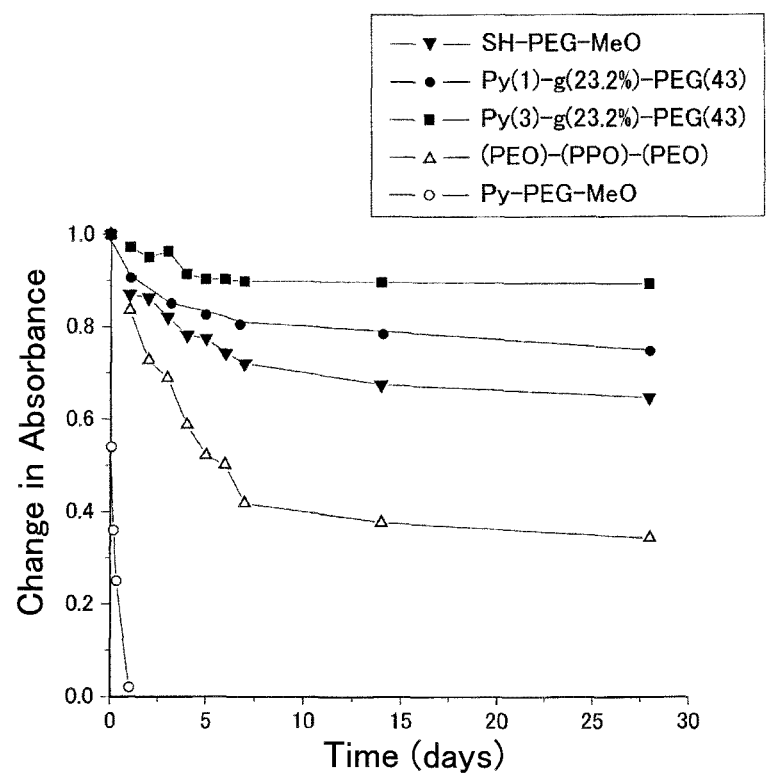
FIG. 9 is a graph showing dispersion stability (under high ionic strength condition) of gold nanoparticles of the present invention.

[Evaluation of Dispersion Stability of Gold Nanoparticles]
Under High Ionic Strength Condition Chloroauric acid (manufactured by Aldrich Co.) was mixed in an amount of 0.2 mM to the polymer micelle solution (0.2 mg/ml, 3 ml) formed from the surface modifier synthesized by the method of Synthesis Example 4, 5, or 7, PEO-PPO-PEO (article name: Pluronic), and SH-PEG-MeO (manufactured by NOF Co., No. 4E4E0F02) and stirred at room temperature for 24 hours. Then, 50 μl (0.1 mg/ml) of aqueous hydrazine solution (manufactured by WAKO Co.) was added thereto as a reducing agent and allowed to react. Next, sodium chloride (manufactured by WAKO Co.) was added in an amount of 1 mg/ml to each reacted solution, thereby obtaining test solutions. Dispersion stability of gold nanoparticles was evaluated for these test solutions by measuring absorbance as a function of time at the maximum absorption wavelength (540 nm) of gold nanoparticles. The results are shown in FIG. 9.

The gold nanoparticles prepared using Py(3)-g(23.2%)-PEG of the surface modifier of the present invention were stable under high ionic strength condition for one month. They exhibited more excellent dispersion stability than that of gold nanoparticles prepared using a typical surface modifier such as PEO-PPO-PEO and SH-PEG-MeO (thiolated polyethylene glycol) as a comparative reference. They were also more stable than gold nanoparticles prepared using Py(1)-g(23.2%)-PEG.

Figure 10:
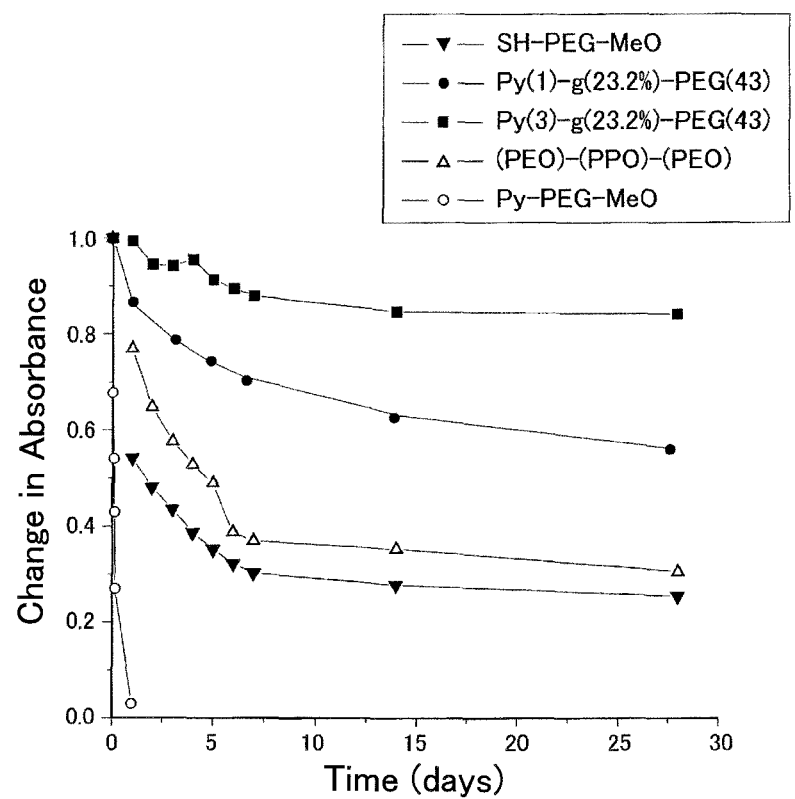
FIG. 10 is a graph showing dispersion stability (under easily-oxidizable condition) of gold nanoparticles of the present invention.

[Evaluation of Dispersion Stability of Gold Nanoparticles]
Under Easily-Oxidizable Condition Chloroauric acid (manufactured by Aldrich Co.) was mixed in an amount of 0.2 mM to the polymer micelle solution (0.2 mg/ml, 3 ml) formed from the surface modifier synthesized by the method of Synthesis Example 4, 5, or 7, PEO-PPO-PEO (article name: Pluronic), and SH-PEG-MeO (manufactured by NOF Co., No. 4E4E0F02) and stirred at room temperature for 24 hours. Then, 50 μl (0.1 mg/ml) of aqueous hydrazine solution (manufactured by WAKO Co.) was added thereto as a reducing agent and allowed to react. Next, oxygen was aerated through each solution after reaction, thereby obtaining test solutions. Dispersion stability of gold nanoparticles was evaluated for these test solutions by measuring absorbance as a function of time at the maximum absorption wavelength (540 nm) of gold nanoparticles. The results are shown in FIG. 10.

The gold nanoparticles prepared using Py(3)-g(23.2%)-PEG of the surface modifier of the present invention were stable under easily-oxidizable condition for one month. They exhibited dispersion stability very superior to that of gold nanoparticles prepared using a typical surface modifier such as PEO-PPO-PEO and SH-PEG-MeO (thiolated polyethylene glycol) as a comparative reference. They were also considerably more stable than gold nanoparticles prepared using Py(1)-g(23.2%)-PEG.

[Measurement of Particle Size]
Comparison of PEG/Py: m=5

Figure 11A:
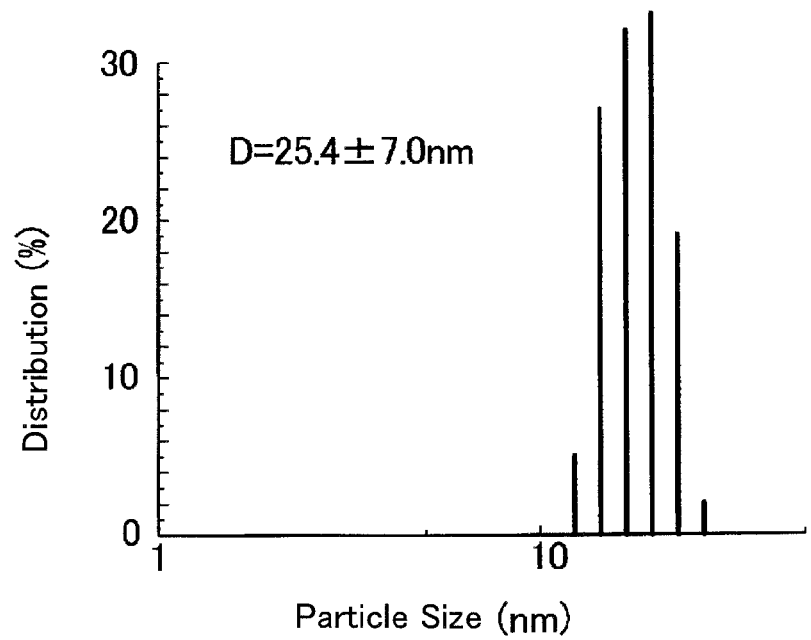
FIG. 11A is a graph showing particle size distribution of polymer micelles formed using a surface modifier of the present invention (m=5, PEG/Py=12.1%)
Figure 11B:
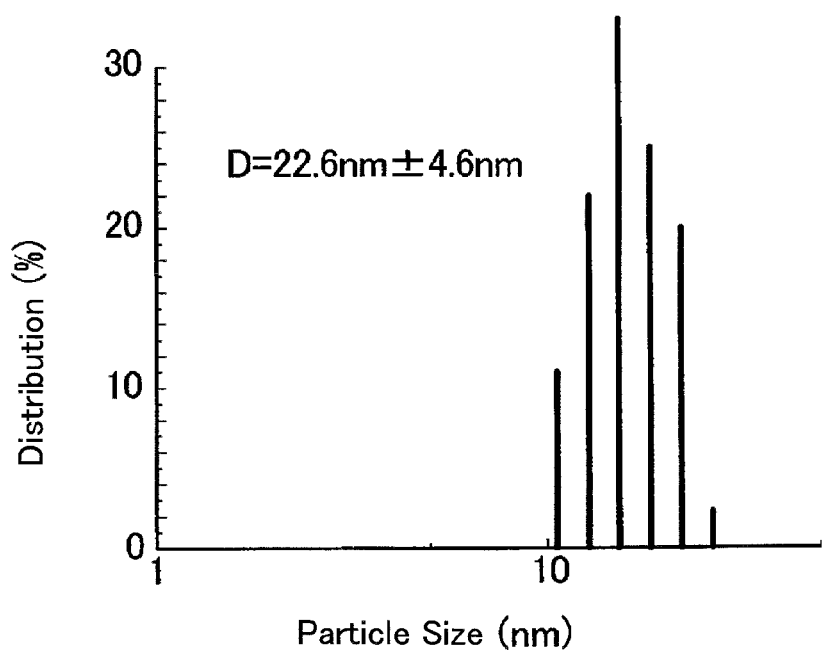
FIG. 11B is a graph showing particle size distribution of polymer micelles formed using a surface modifier of the present invention (m=5, PEG/Py=25.2%)
Figure 11C:
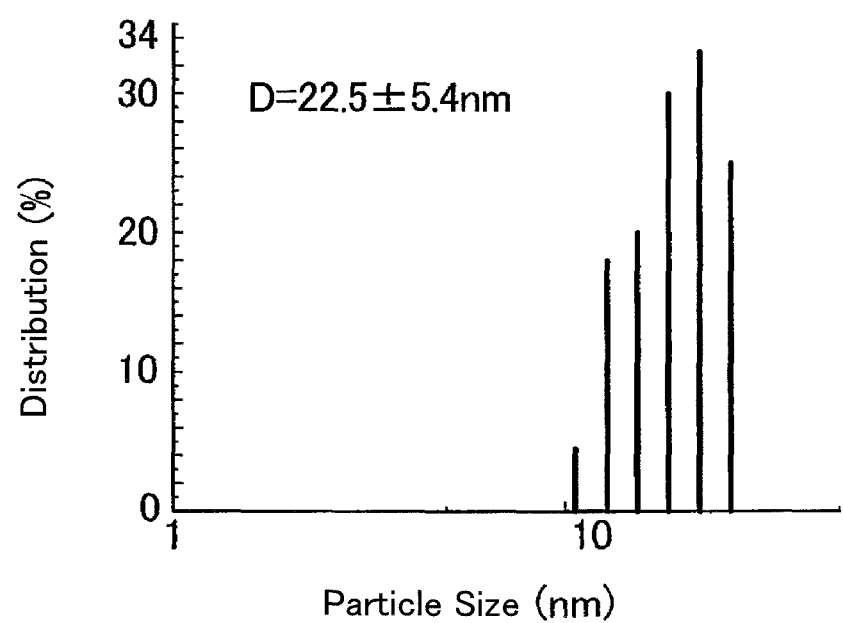
FIG. 11C is a graph showing particle size distribution of polymer micelles formed using a surface modifier of the present invention (m=5, PEG/Py=51.5%)

Polymer micelles were formed using Py(5)-g(12.1%)-PEG, Py(5)-g(25.2%)-PEG, and Py(5)-g(51.5%)-PEG, and their particle sizes were measured by DLS. All polymerization degrees (n) of ethylene glycols were 43. The method for forming the micelles was similar to the method described above. The measurements results by DLS are shown in FIG. 11A (12.1%), FIG. 11B (25.2%), FIG. 11C (51.5%).

As shown in FIG. 11, uniform particles having a particle size of about 20 nm were formed in all micelles regardless of copolymerization ratio (PEG/Py).

[Preparation of Gold Nanoparticles]

Gold nanoparticles were prepared using hydrophobic cores of the polymer micelles formed from Py(5)-g(25.2%)-PEG as a nano-reaction field.

Chloroauric acid (manufactured by Aldrich Co.) was mixed in an amount of 0.2 mM to the polymer micelle solution (0.2 mg/3 ml) formed from Py(5)-g(25.2%)-PEG and stirred at room temperature for 24 hours. Then, 50 μl (0.1 mg/ml) of aqueous hydrazine solution (manufactured by WAKO Co.) was added thereto as a reducing agent and allowed to react.

[Measurement of Particle Size of Gold Nanoparticles]

Figure 12:
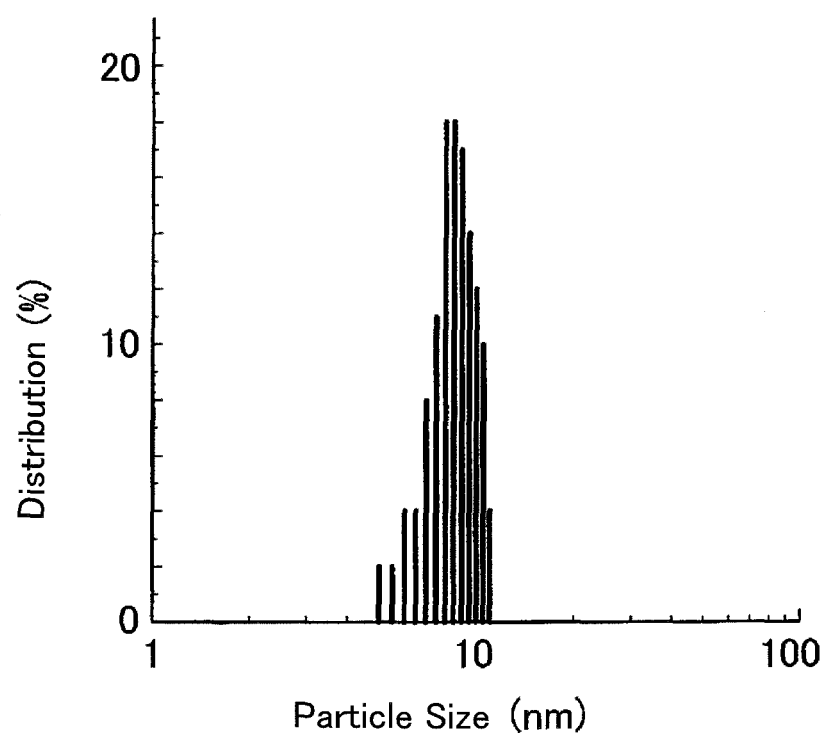
FIG. 12 is a view showing particle size distribution of gold nanoparticles of the present invention (m=5, PEG/Py=25.2%)
Figure 13:
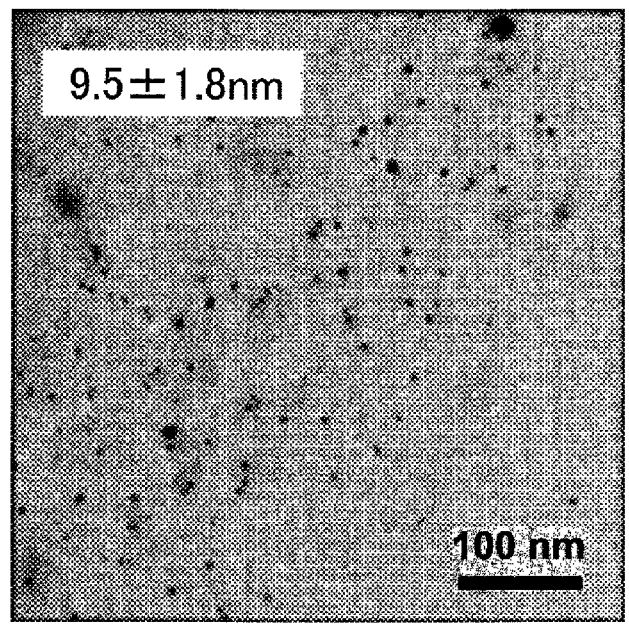
FIG. 13 is a view showing a TEM image of gold nanoparticles of the present invention (m=5, PEG/Py=25.2%)

Particle sizes of the gold nanoparticles resulting from the method described above were measured by DLS and TEM. The measurement results by DLS are shown in FIG. 12 and the measurement results by TEM are shown in FIG. 13. As a result, it was confirmed that relatively monodisperse gold nanoparticles having an average particle size of 9.5±1.8 nm were generated.

Figure 14:
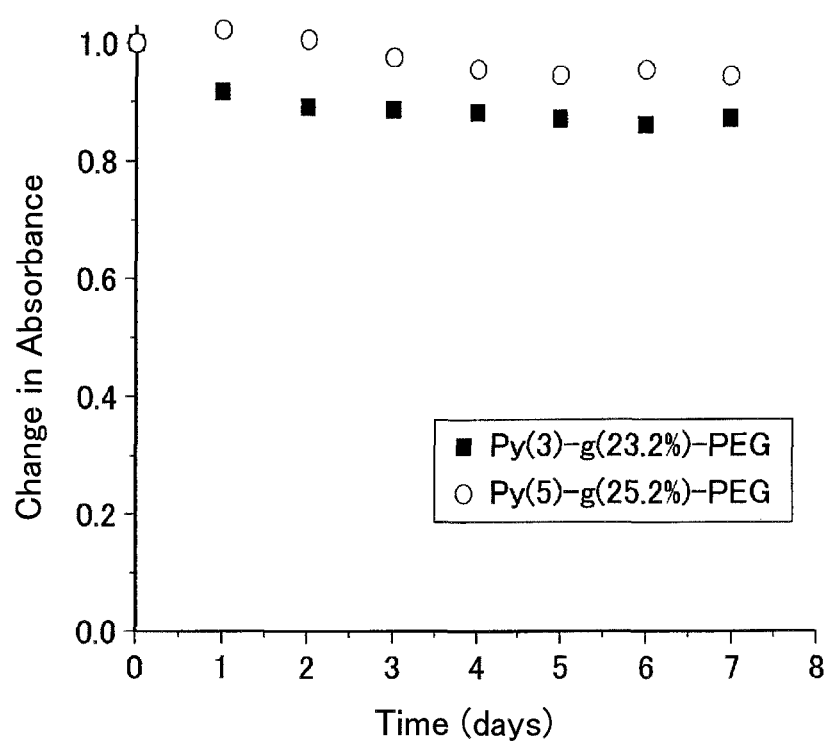
FIG. 14 is a graph showing dispersion stability (under high ionic strength condition) of gold nanoparticles of the present invention.

[Evaluation of Dispersion Stability of Gold Nanoparticles]
Under High Ionic Strength Condition Chloroauric acid (manufactured by Aldrich Co.) was mixed in an amount of 0.2 mM to the polymer micelle solution (0.2 mg/ml, 3 ml) of Py(3)-g(23.2%)-PEG or Py(5)-g(25.2%)-PEG formed from the surface modifier Py(3)-g(23.2%)-PEG or Py(5)-g(25.2%)-PEG of the present invention and stirred at room temperature for 24 hours. Then, 50 μl (0.1 mg/ml) of the aqueous hydrazine solution (manufactured by WAKO Co.) was added thereto as a reducing agent and allowed to react. Next, sodium chloride (manufactured by WAKO Co.) was added in an amount of 1 mg/ml to each reacted solution, thereby obtaining test solutions. Dispersion stability of gold nanoparticles was evaluated for these test solutions by measuring absorbance as a function of time at the maximum absorption wavelength (540 nm) of gold nanoparticles. The results are shown in FIG. 14.

The gold nanoparticles prepared using Py(5)-g(25.2%)-PEG of the surface modifier of the present invention were stable under high ionic strength condition for one week. They also exhibited excellent dispersion stability in comparison with the gold nanoparticles prepared using Py(3)-g(23.2%)-PEG.

Figure 15:
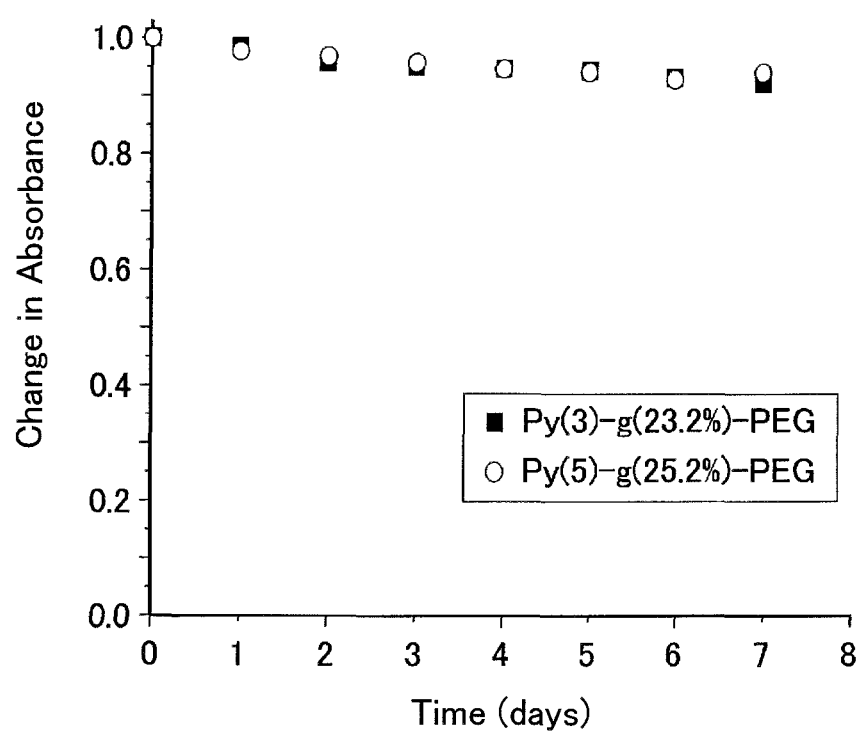
FIG. 15 is a graph showing dispersion stability (under easily-oxidizable condition) of gold nanoparticles of the present invention.

[Evaluation of Dispersion Stability of Gold Nanoparticles]
Under Easily-Oxidizable Condition Chloroauric acid (manufactured by Aldrich Co.) was mixed in an amount of 0.2 mM to the polymer micelle solution (0.2 mg/ml, 3 ml) of Py(3)-g(23.2%)-PEG or Py(5)-g(25.2%)-PEG formed from the surface modifier Py(3)-g(23.2%)-PEG or Py(5)-g(25.2%)-PEG of the present invention and stirred at room temperature for 24 hours. Then, 50 μl (0.1 mg/ml) of the aqueous hydrazine solution (manufactured by WAKO Co.) was added thereto as a reducing agent and allowed to react. Next, oxygen was aerated through each solution after reaction, thereby obtaining test solutions. Dispersion stability of gold nanoparticles was evaluated for these test solutions by measuring absorbance as a function of time at the maximum absorption wavelength (540 nm) of gold nanoparticles. The results are shown in FIG. 15.

The gold nanoparticles prepared using Py(5)-g(25.2%)-PEG of the surface modifier of the present invention were stable under easily-oxidizable condition for one week. They also exhibited excellent dispersion stability in comparison with the gold nanoparticles prepared using Py(3)-g(23.2%)-PEG.

Synthesis of Polymerizable Monomer (A1)

Under argon atmosphere, 20 ml of dehydrated dichloromethane (manufactured by WAKO Co.) was added to 12.0 g (200 mmol) of ethylene glycol (manufactured by Aldrich Co.) represented by formula (11). Next, 380 mg (2 mmol) of p-toluenesulfonic acid monohydrate (TsOH.H₂O) (manufactured by Aldrich Co.) was added thereto, to which then 8.41 g (100 mmol) of 3,4-dihydro-2H-pyran (manufactured by Aldrich Co.) was added through a dropping funnel over 10 minutes and stirred for one hour. Then, a small amount of triethylamine (TEA) (manufactured by WAKO Co.) was added thereto to stop the reaction and also a saturated aqueous sodium hydrogen carbonate solution was added thereto, which was then extracted 3 times with chloroform (manufactured by WAKO Co.), followed by concentrating. The concentrated liquid was purified by column chromatography (column: silica (manufactured by WAKO Co.), solvent: ethyl acetate/hexane=2/1) to obtain the compound represented by formula (12) (yield amount: 6.72 g, yield rate: 23%). The reaction scheme is shown below.

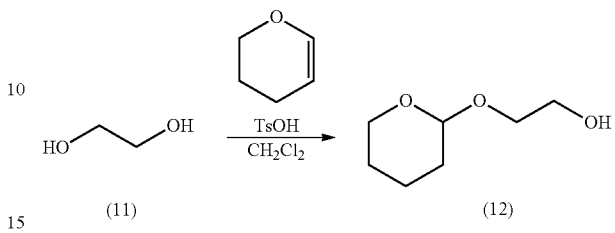

The compound represented by formula (12) of 146 mg (1 mmol) was subjected to argon replacement, to which then 15 ml of distilled tetrahydrofuran (THF) (manufactured by WAKO Co.) was introduced under argon flow and a THF solution (1.1 mmol) of potassium naphthalene (manufactured by Aldrich Co.) was introduced. Ethylene oxide of 2.5 ml (50 mmol) (manufactured by Sumitomo 3M Ltd.) cooled in liquid nitrogen was collected into a polymerization vessel by a pre-cooled syringe and stirred for 2 days. Reprecipitation was then performed with diisopropyl ether (manufactured by WAKO Co.) to obtain THP-PEG-OH represented by formula (13) (yield amount: 2.09 g, yield rate: 95%). The reaction scheme is shown below.

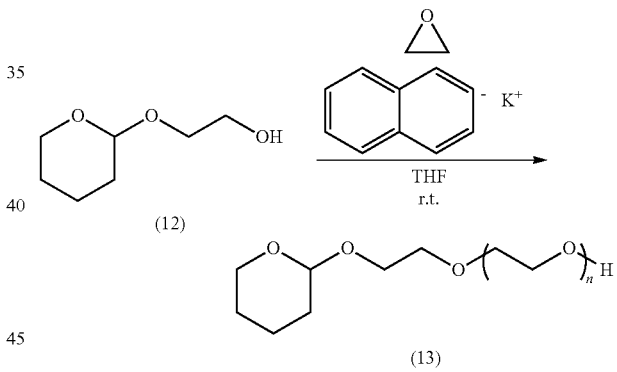

After dehydrated THF was added to 3-bromo-1-propanol (500 mmol) previously subjected to argon replacement, 120 g (500 mmol) of sodium azide was added thereto and stirred for 120 minutes thereby to obtain azide propanol represented by formula (14). The azide propanol of 13.7 g (135 mmol) was subjected to argon replacement, to which then 250 ml of dehydrated THF was added. Then, 20.6 ml (148 mmol) of TEA and 11.5 ml (148 mmol) of p-toluenesulfonyl chloride (MsCl) (manufactured by Aldrich Co.) were added thereto and stirred for one hour. After Celite filtration, rinse with aqueous sodium hydrogen carbonate solution, extraction with ethyl acetate (manufactured by WAKO Co.), and dehydration with dehydrated magnesium sulfate (manufactured by WAKO Co.) were carried out, followed by concentration, to obtain the compound represented by formula (15) (yield amount: 24.0 g, yield rate: 99%). Here, n (number-average polymerization degree) was 56.

The reaction scheme is shown below.

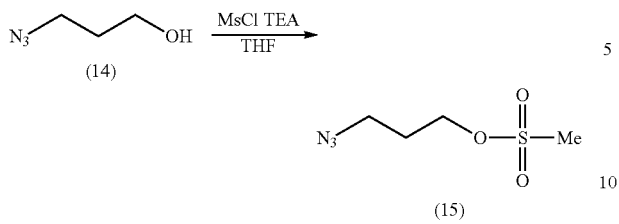

After 6 ml of dehydrated THF was added to 300 mg (0.15 mmol) of THP-PEG-OH previously subjected to argon replacement and represented by formula (13), 1.18 mg (0.75 mmol) of sodium hydride (NaH) (manufactured by WAKO Co.) was added thereto and stirred for 15 minutes. Mesyl azide propane ether of 1.269 mg (1.5 mmol) represented by formula (15) was added thereto and stirred for one day. After Celite filtration, reprecipitation with 30 times amount of diisopropyl ether (DIPE) (manufactured by WAKO Co.) and vacuum-freeze drying were performed, thereby collecting THP-PEG-N₃ represented by formula (16) (yield amount: 286 mg, yield rate: 92%). The reaction scheme is shown below.

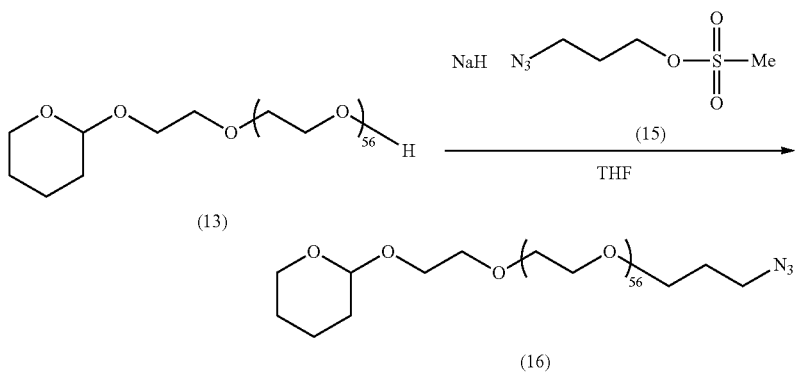

Under argon atmosphere, 250 mg (0.125 mmol) of THP-PEG-N₃ represented by formula (16) was dissolved in 30 ml of methanol (MeOH) (manufactured by WAKO Co.), to which then 2.4 mg (0.0125 mmol) of p-toluenesulfonic acid (TsOH) (manufactured by WAKO Co.) was added and stirred for one day. Then, the material thus obtained was concentrated, added with aqueous sodium hydrogen carbonate solution, and extracted 4 times with dichloromethane (manufactured by WAKO Co.). After further concentration, the material thus obtained was diluted with benzene (manufactured by WAKO Co.) and subjected to reprecipitation with 30 times amount of DIPH and vacuum-freeze drying, thereby obtaining OH-PEG-N₃ represented by formula (17) (yield amount: 231 mg, yield rate: 91%). The reaction scheme is shown below.

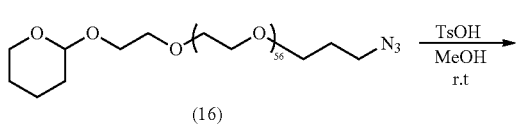

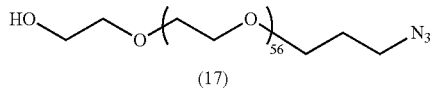

After dehydrated THF was added to 200 mg (0.1 mol) of OH-PEG-N₃ previously subjected to argon replacement and represented by formula (17), 12 mg (0.5 mmol) of NaH was added thereto and stirred for 15 minutes. Distilled anhydrous methacrylic acid of 298 μl (2 mmol) (manufactured by Aldrich Co.) was added thereto and stirred for one day. After Celite filtration, reprecipitation and purification with 30 times amount of DIPE and followed by vacuum-freeze drying were performed, thereby collecting the compound represented by formula (18) (yield amount: 185 mg, yield rate: 91%). The reaction scheme is shown below.

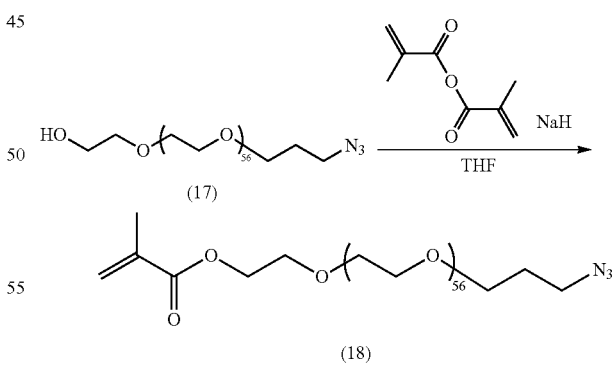

[Synthesis of Polymerizable Monomer (B1)]
Synthesis of 4-Pyridinepropanol-Methacrylate After 6.85 g (50 mmol) of 4-pyridinepropanol (manufactured by Aldrich Co.) represented by formula (19), 4.73 g (55 mmol) of methacrylic acid (manufactured by Aldrich Co.) represented by formula (20), and 740 mg (5 mmol) of 4-(1-pyrrolidinyl)pyridine (manufactured by Aldrich Co.) were dissolved in 100 ml of dehydrated dichloromethane (manufactured by WAKO Co.), 11.3 g (55 mmol) of N,N'-dicyclohexylcarbodiimide (DCC) (manufactured by Aldrich Co.) was added thereto and allowed to react at room temperature for 1 hour. Then, insoluble urea was removed by filtration, followed by removal of solvent under reduced pressure. The residual material was purified by column chromatography (column: silica (manufactured by WAKO Co.), solvent: hexane/ethyl acetate) to obtain 4-pyridinepropanol-methacrylate represented by formula (21) (yield amount: 8.5124 g, yield rate: 82.8%). The reaction scheme is shown below.

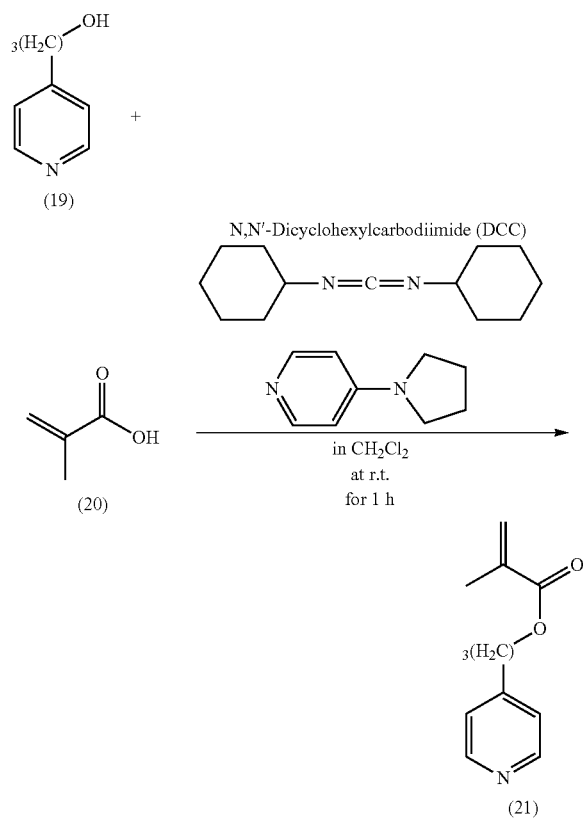

[Synthesis of Graft Copolymer (Py-g-PEG)]

The compound (polymerizable monomer (A1)) of 800 mg (0.33 mmol) resulting from the synthesis method described above and represented by formula (18), 228 mg (1 mmol) of 4-pyridinepropanol-methacrylate (polymerizable monomer (B1)) resulting from the synthesis method described above and represented by formula (21), and 1.6 mg (0.01 mmol) of AIBN were dissolved in 10 ml of DMF and subjected to 3 cycles of freeze-degassing. Then, the material thus obtained was stirred at 60° C. for 24 hours. Followed by reprecipitation with 20 times amount of solvent (diethyl ether (manufactured by Aldrich Co.)/isopropyl alcohol (manufactured by WAKO Co.)=20/1 in volume ratio) and vacuum-freeze drying, thereby collecting the graft copolymer (Py(3)-g(25.8%)-PEG) represented by formula (22) (yield amount: 638 mg, yield rate: 62%). Here, "Py(3)" indicates that the carbon number of alkylene group of $R^{2b}$ of the polymerizable monomer (B1) represented by general formula (V) is 3, and "g(25.8%)" indicates that the copolymerization ratio of polyethylene glycol (PEG) to pyridine (Py) is 25.8%. The reaction scheme is shown below.

[Synthesis of Lac-Propargyl]

Pyridine (manufactured by WAKO Co.) of 141 ml (1.75 mol) in 24 equivalents and 166 ml (1.75 mol) of acetic acid anhydride (manufactured by WAKO Co.) were added to D-lactose (manufactured by Aldrich Co.) represented by formula (23) and stirred at room temperature for 3 days. After Celite filtration, the material thus obtained was subjected to concentration and vacuum drying and then dissolved in chloroform. Diethyl ether was slowly added thereto within an ice bath until crystal deposition. The crystal was dissolved again in chloroform and then diethyl ether was slowly added until crystal deposition. The material thus obtained was vacuum-dried to obtain Ac-lactose represented by formula (24).

Next, 40 ml of dehydrated dichloromethane was added to 10 g (14.4 mmol) of Ac-lactose represented by formula (24) under argon atmosphere and cooled to 0° C. Propargyl alcohol of 991 mg (17.6 mmol) (manufactured by WAKO Co.) was added thereto and 5.91 ml (44.1 mmol) of boron trifluoride diethyl ether (manufactured by WAKO Co.) of 3 equivalents based on Ac-lactose was slowly added dropwise thereto and stirred at 0° C. for one hour, followed by stirring at room temperature for one day. The material thus obtained was diluted with chloroform, rinsed with water, aqueous sodium hydrogen carbonate solution, and brine in sequence, and added with dehydrated magnesium sulfate, and concentrated after filtration. The material thus obtained was dissolved in a small amount of DMF, to which then 678 mg (7.35 mmol) of hydrazine acetate (manufactured by WAKO Co.) of 0.5 equivalent was added at 60° C. under argon atmosphere and stirred for 30 minutes. The material thus obtained was added with a small amount of aqueous sodium hydrogen carbonate solution and diluted with water, then extracted 3 times with ethyl acetate, rinsed with water 3 times and brine, added with dehydrated magnesium sulfate, and concentrated after filtration. The material thus obtained was purified by column chromatography (column: silica (manufactured by WAKO Co.), solvent: ethyl acetate/hexane=3/4) to obtain Ac-lactose-propargyl represented by formula (25) after vacuum drying.

Next, 1.65 g (2.43 mmol) of the Ac-lactose-propargyl represented by formula (25) was added to 8 ml of methanol and 262 mg (4.86 mmol) of sodium methoxide (manufactured by Aldrich Co.) under argon atmosphere and stirred for one day. The material thus obtained was added with a cation exchange resin and subjected to Celite filtration and mild concentration, and then added with diethyl ether until crystal deposition. Then, filtration and vacuum drying was performed to obtain Lac-propargyl represented by formula (26) (yield amount: 836 mg, yield rate: 33% (final product)). The reaction scheme is shown below.

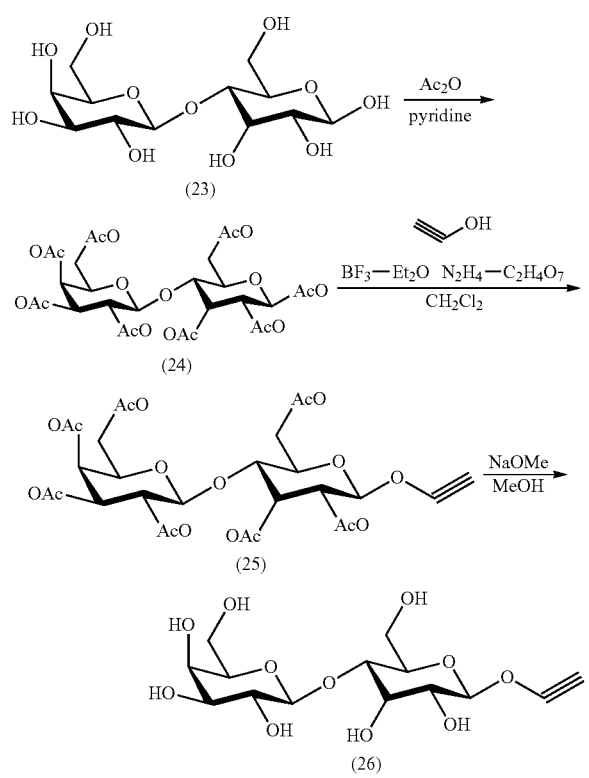

[Synthesis of Lactose-Modified Graft Copolymer]

The graft copolymer (Py(3)-g(25.8%)-PEG) of 200 mg (0.008 mmol) resulting from the synthesis method described above and represented by formula (22) and 135 mg (0.37 mmol) of Lac-propargyl represented by formula (26) were dissolved in 7 ml of t-butyl alcohol (manufactured by WAKO Co.) and 4 ml of water. Copper sulfate (II) pentahydrate of 18.2 mg (0.073 mmol) (manufactured by WAKO Co.) and 28.9 mg (0.146 mmol) of sodium ascorbate (manufactured by WAKO Co.) were respectively dissolved in 1.5 ml of water, then added thereto and stirred for 2 days. After concentration thereof and dialysis treatment for 5 days followed by vacuum-freeze drying, Py(3)-g(25.8%)-PEG-Lactose represented by formula (27) was collected (yield amount: 205 mg, yield rate: 92%). The reaction scheme is shown below.

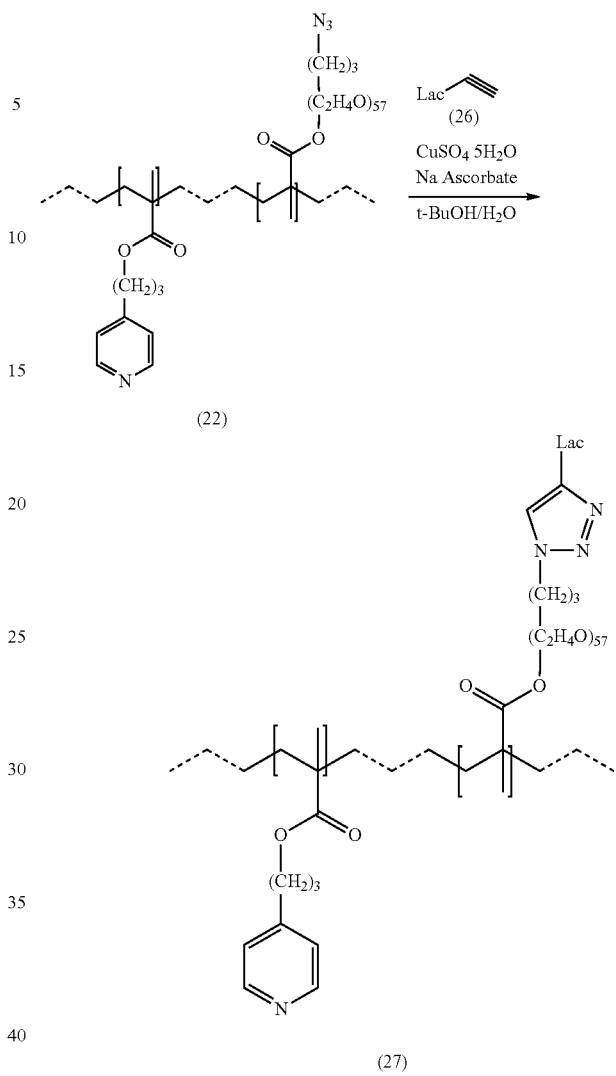

[Investigation of Selective Aggregation]

Gold nanoparticles were prepared using hydrophobic cores of the polymer micelles formed from Py(3)-g(25.8%)-PEG-Lactose and Py(3)-g(25.8%)-PEG-Mannose as a nano-reaction field. Gold Nanoparticles (5 nm) Having Lactose at Surface Micelles were formed by dissolving Py(3)-g(25.8%)-PEG-Lactose in N,N-dimethylacetamide (DMA) (manufactured by WAKO Co.), introducing it into a dialysis membrane (molecular weight cut off: about 10,000), and dialyzing against water in 300 times amount of DMA for 4 days. Chloroauric acid (manufactured by Aldrich Co.) was mixed in an amount of 0.2 mM to 3 ml (0.2 mg/ml) of the micelle solution and stirred at room temperature for 24 hours. Then, 50 μl (0.1 mg/ml) of aqueous hydrazine solution (manufactured by WAKO Co.) was added thereto as a reducing agent and allowed to react. Gold Nanoparticles (40 nm) Having Lactose at Surface Micelles were formed by dissolving Py(3)-g(25.8%)-PEG-Lactose in DMA, introducing the material thus obtained into a dialysis membrane (molecular weight cut off: about 10,000), and dialyzing against water in 300 times amount of DMA for 4 days. Chloroauric acid (manufactured by Aldrich Co.) was mixed in an amount of 0.6 mM to 3 ml (0.2 mg/ml)

of the solution thus obtained and stirred at room temperature for 24 hours. Then, 50 µl (0.1 mg/ml) of aqueous hydrazine solution (manufactured by WAKO Co.) was added thereto as a reducing agent and allowed to react.

Gold Nanoparticles (40 nm) Having Mannose at Surface

Micelles were formed by dissolving Py(3)-g(25.8%)-PEG-Mannose in DMA, introducing it into a dialysis membrane (molecular weight cut off: about 10,000), and dialyzing against water in 300 times amount of DMA for 4 days. Chloroauric acid (manufactured by Aldrich Co.) was mixed in an amount of 0.6 mM to 3 ml (0.2 mg/ml) of the solution thus obtained and stirred at room temperature for 24 hours. Then, 50 µl (0.1 mg/ml) of aqueous hydrazine solution (manufactured by WAKO Co.) was added thereto as a reducing agent and allowed to react. Here, Py(3)-g(25.8%)-PEG-Mannose was obtained through modifying a sugar chain by a method similar to that of Py(3)-g(25.8%)-PEG-Lactose.

Aggregation of the gold nanoparticles prepared by the method described above was confirmed by a transmission electron microscope (TEM) (HITACHI H-9500, manufactured by HITACHI Ltd.)

Figure 16A:
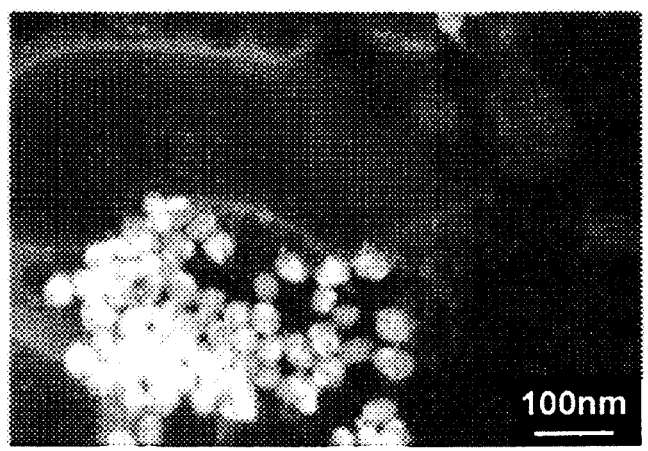
FIG. 16A is a view showing selective aggregation (TEM images) of a graft copolymer of the present invention.

When RCA 120 lectin in a concentration of 20 mg/ml was added to the gold nanoparticles (40 nm) having lactose a: the surface and the gold nanoparticles (5 nm) having lactose at the surface, the aggregation after 8 hours was a mixed aggregation of the gold nanoparticles (40 nm) having lactose at the surface and the gold nanoparticles (5 nm) having lactose at the surface (FIG. 16A).

Figure 16B:
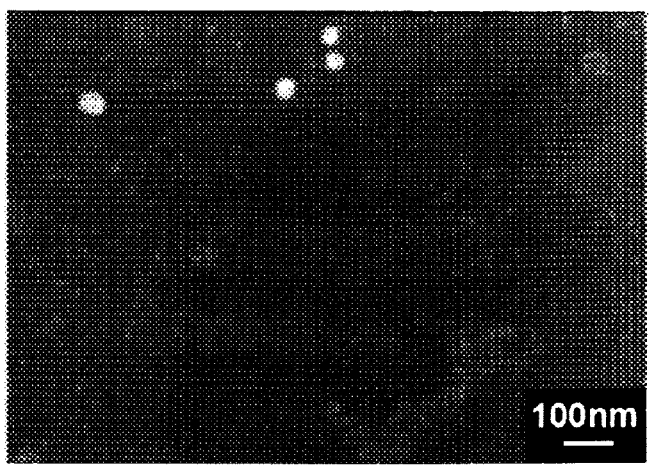
FIG. 16B is a view showing selective aggregation (TEM images) of a graft copolymer of the present invention.

When RCA 120 lectin in a concentration of 20 mg/ml was added to the gold nanoparticles (40 nm) having mannose at the surface and the gold nanoparticles (5 nm) having lactose at the surface, the aggregation after 8 hours was a selective aggregation of only the gold nanoparticles (5 nm) having lactose at the surface (FIG. 16B).

Figure 16C:
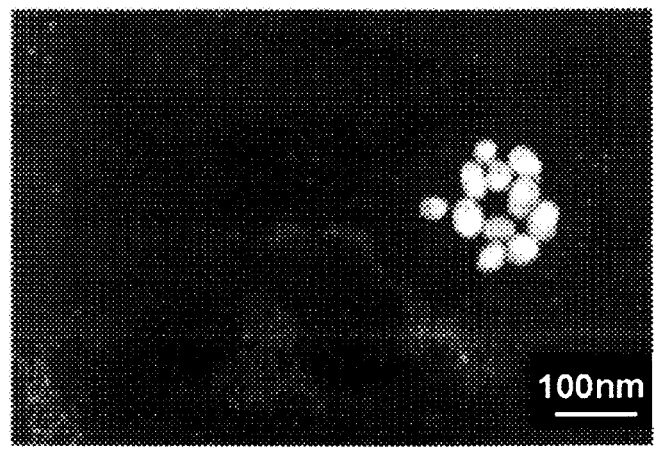
FIG. 16C is a view showing selective aggregation (TEM images) of a graft copolymer of the present invention.

When RCA 120 lectin in a concentration of 20 mg/ml and Con A lectin in a concentration of 20 mg/ml were added to the gold nanoparticles (40 nm) having mannose at the surface and the gold nanoparticles (5 nm) having lactose at the surface, the aggregation after 8 hours was a selective aggregation such that an aggregation of only the gold nanoparticles (40 nm) having mannose at the surface and an aggregation of only the gold nanoparticles (5 nm) having lactose at the surface were separately formed (FIG. 16C).

Investigation of Sugar-Recognition Ability

Gold nanoparticles were prepared using hydrophobic cores of the polymer micelles formed from Py(3)-g(25.8%)-PEG-Lactose resulting from the synthesis method described above as a nano-reaction field. The preparation method was similar to those described above.

Micelles were formed by dissolving Py(3)-g(25.8%)-PEG-Lactose in N,N-dimethylacetamide (DMA) (manufactured by WAKO Co.), introducing it into a dialysis membrane (molecular weight cut off: about 10,000), and dialyzing against water in 300 times amount of DMA for 4 days. Chloroauric acid (manufactured by Aldrich Co.) was mixed in an amount of 0.2 mM to 3 ml (0.2 mg/ml) of the micelle solution and stirred at room temperature for 24 hours. Then, 50 µl (0.1 mg/ml) of aqueous hydrazine solution (manufactured by WAKO Co.) was added thereto as a reducing agent and allowed to react.

RCA 120 lectin of 5, 10, 20, or 50 mg/ml (manufactured by WAKO Co.), which is a lectin specifically recognizing galactose, was added to a dispersion of gold nanoparticles coated with Py(3)-g(25.8%)-PEG-Lactose, and UV spectra thereof after 8 hours were measured by an ultraviolet-visible absorption spectrophotometer (Agilent 8453A Diod Array, manufactured by Agilent Co.) (see FIG. 17).

Figure 17:
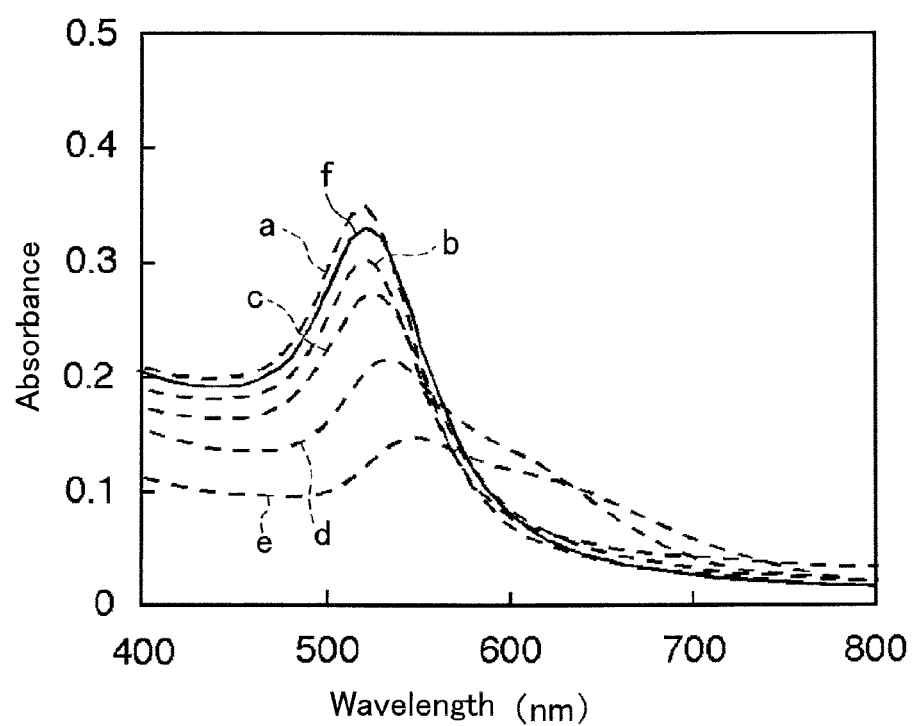
FIG. 17 is a graph showing sugar-recognition ability (UV spectra) of a graft copolymer of the present invention.

Marks of a to f in FIG. 17 indicate the following various solutions; a: non-addition, b: 5 mg/ml addition, c: 10 mg/ml addition, d: 20 mg/ml addition, e: 50 mg/ml addition of RCA 120 lectin respectively, f: addition of excessive amount of lactose and redispersion.

The gold nanoparticles coated with Py(3)-g(25.8%)-PEG-Lactose were initially in a dispersed state but agglomerated by addition of RCA 120 lectin and redispersed by addition of free lactose in an excessive amount.

Change of absorbance from a to e indicates that gold nanoparticles in a dispersed state have agglomerated by interaction between lactose and lectin at the surface of the nanoparticles. Furthermore, change of absorbance from e to f indicates that gold nanoparticles have redispersed by addition of free lactose. It is understood from these facts that sugar-recognition ability on the basis of the graft copolymer of the present invention is reversible.

[Investigation of Aggregation]

Synthesis of Chain Transfer Agent (CDB)

Magnesium (12.7 mmol, 310 mg) was sufficiently stirred within a two-diameter recovery flask under reduced pressure, which was then subjected to Ar replacement and THF addition. Bromobenzene (12.7 mmol, 1 eq, 1.33 ml) represented by formula (28) was slowly added thereto and stirred at room temperature for one hour and at 60° C. for 15 minutes. Next, carbon bisulfide (14.0 mmol, 1.1 eq, 846 µl) was slowly added thereto within an ice bath and stirred at 0° C. for 1.5 hours and at room temperature for 30 minutes. The material thus obtained was put into ice water and subjected to acidification with 1N HCl and extraction with diethyl ether. The material thus obtained was subjected to drying with $MgSO_4$ and filtration, and then concentration and vacuum drying (formation of DTBA represented by formula (29)). DTBA (6.13 mmol, 946 mg) was dissolved in $CCl_4$ and put into a two-diameter recovery flask, then α-methylstyrene (9.19 mmol, 1.5 eq, 1.19 ml) and tosic acid monohydrate (290 mg) were added thereto and heated to reflux overnight under Ar atmosphere. The reactant was diluted with chloroform and rinsed twice with $NaHCO_3$ (aq) and once with NaCl(aq). The material thus obtained was further subjected to drying with $MgSO_4$ and filtration, and then concentration and vacuum drying. The crude product was directed to a column (Hexane) and subjected to concentration and vacuum drying, thereby obtaining CDB represented by formula (30). The reaction scheme is shown below.

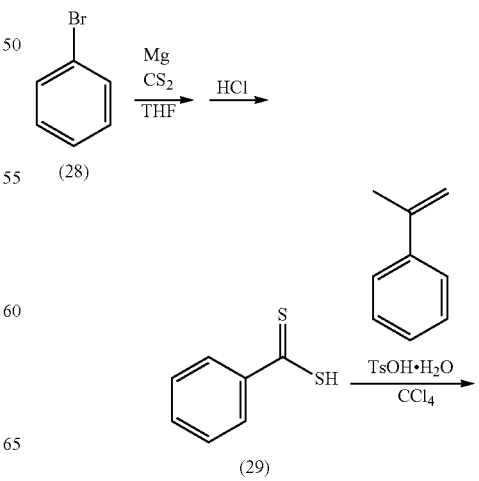

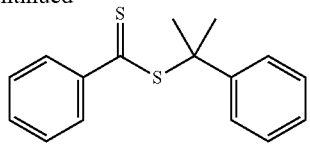

(30)

¹H NMR results of CDB are shown below.
¹H NMR (CDCl₃): δ
7.85 (2H, dd, J=8.2, 1.2 Hz)
7.56-7.54 (2H, m)
7.47 (1H, dq, J=11.4, 2.7 Hz)
7.34-7.30 (4H, m)
7.22 (1H, tt, J=7.3, 1.3 Hz)
2.01 (6H, s)

Synthesis of Graft Copolymer (Py-g-PEG)

4-Pyridinepropanol-methacrylate (polymerizable monomer (B1)) resulting from the synthesis method described above and represented by formula (21), the compound represented by formula (31) (polymerizable monomer (A): Hetero-PEG), the compound represented by formula (32) (polymerizable monomer (A): MeO-PEG), CDB represented by formula (30) as a chain transfer agent, and AIBN were dissolved in DMF and subjected to 3 cycles of freeze-degassing. The material thus obtained was then stirred at 60° C. for 24 hours. Reprecipitation with 20 times amount of solvent (diethyl ether (manufactured by Aldrich Co.)/isopropyl alcohol (manufactured by WAKO Co.)=20/1 in volume ratio) and vacuum-freeze drying were then performed, thereby collecting the graft copolymer (Py-g-PEG) represented by formula (33). The reaction scheme is shown below. The composition of the synthesized graft copolymer (Py-g-PEG) is also shown in Table 4.

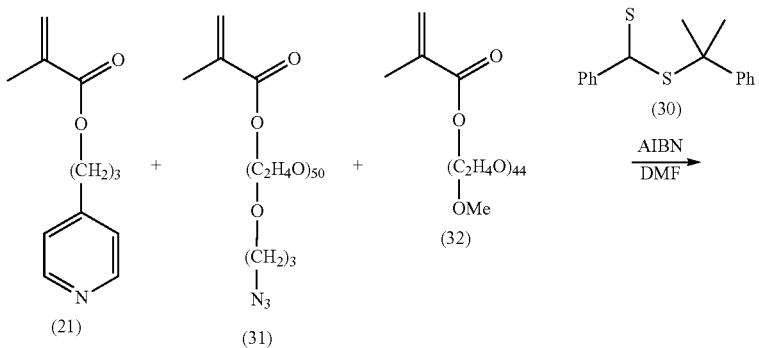

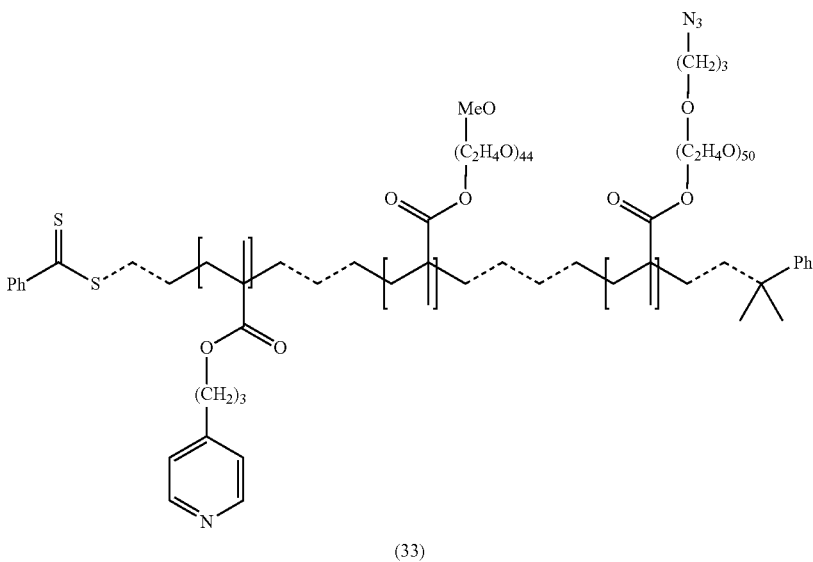

TABLE 4

| | Constitutional Rate (parts by mass) | | |
|---|---|---|---|
| | Py | MeO-PEG | Hetero-PEG |
| Py-g-PEG(A) | 100 | 0 | 30.0 |
| Py-g-PEG(B) | 100 | 7.5 | 22.5 |
| Py-g-PEG(C) | 100 | 15.0 | 15.0 |
| Py-g-PEG(D) | 100 | 22.5 | 7.5 |
| Py-g-PEG(E) | 100 | 30.0 | 0 |

[Synthesis of Lactose-Modified Graft Copolymer]

The graft copolymer (Py-g-PEG) resulting from the synthesis method described above and represented by formula (33) and Lac-propargyl represented by formula (26) were dissolved in water. Copper sulfate (II) pentahydrate (manufactured by WAKO Co.) and sodium ascorbate (manufactured by WAKO Co.) were respectively dissolved in water, then added thereto and stirred for 2 days. After concentration thereof and dialysis treatment for 5 days followed by vacuum-freeze drying, Py-g-PEG-Lactose represented by formula (34) was collected. The reaction scheme is shown below. Furthermore, number-average molecular weight (Mn), dispersion degree (Mw/Mn), copolymerization ratio (PEG/Py) of PEG to Py, unit number of PEG and Py, and rate of Hetero-PEG and MeO-PEG of the synthesized graft copolymer (Py-g-PEG) are shown in Table 5. Here, number-average molecular weight (Mn) and dispersion degree (Mw/Mn) were measured by gel permeation chromatography (GPC), and copolymerization ratio (PEG/Py) of PEG to Py, unit number of PEG and Py, and rate of Hetero-PEG and MeO-PEG were measured by NMR.

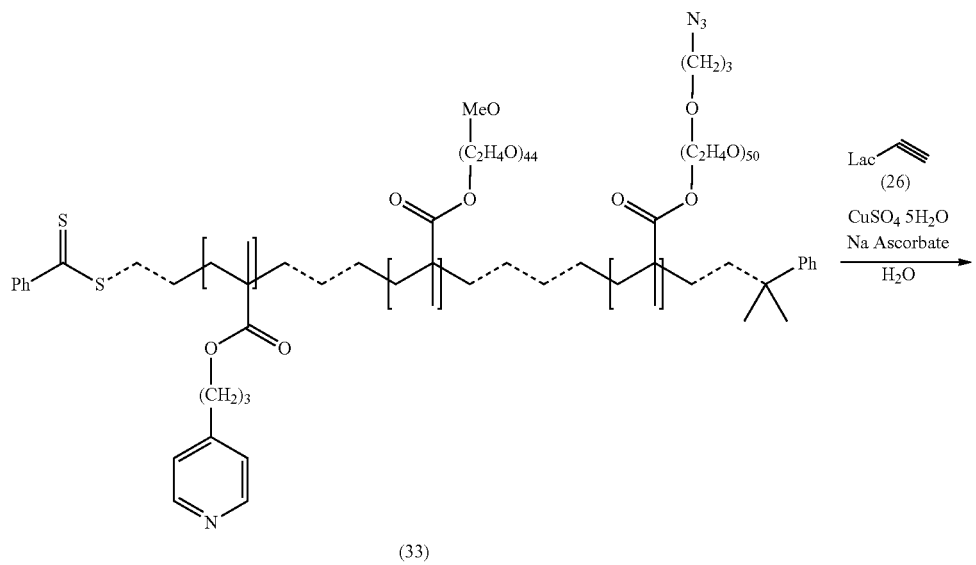

(33)

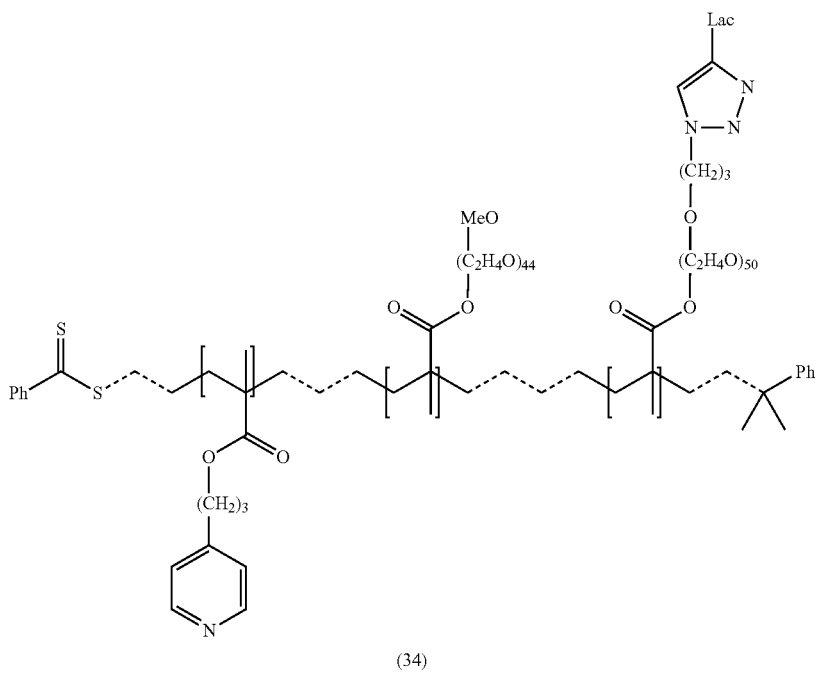

(34)

TABLE 5

|  | Mn | Mw/Mn | Copolymerization Ratio of PEG to Py (PEG/Py) | Unit Number of PEG and Py (PEG. Py) | Rate (%) (Hetero-PEG. MeO-PEG) |
|---|---|---|---|---|---|
| Py-g-PEG-Lac(A) | 16834 | 1.30 | 0.18 | (29. 5.2) | (100. 0) |
| Py-g-PEG-Lac(B) | 15201 | 1.47 | 0.19 | (26.1. 4.8) | (79. 21) |
| Py-g-PEG-Lac(C) | 13863 | 1.40 | 0.18 | (23.8. 4.3) | (47. 53) |
| Py-g-PEG-Lac(D) | 15547 | 1.42 | 0.18 | (26.7. 4.9) | (28. 72) |
| Py-g-PEG-Lac(E) | 16834 | 1.28 | 0.17 | (28.9. 5.3) | (0. 100) |

Preparation of Gold Nanoparticles

Figure 18:
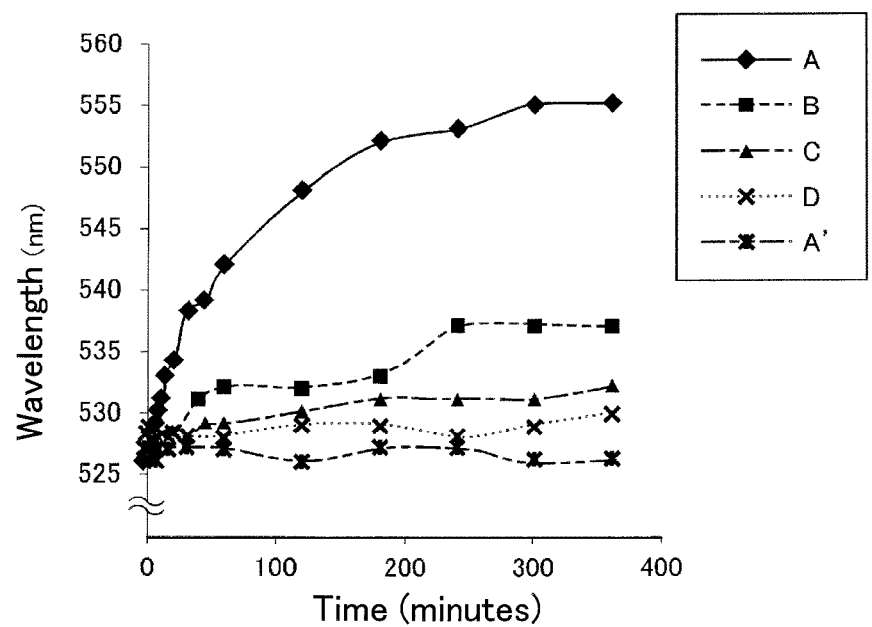
FIG. 18 is a graph showing aggregation (UV spectra) of a graft copolymer of the present invention.

Py-g-PEG-Lactose (0.5 mg/ml) of 4 ml shown in Table 5 was added to 16 ml of a gold colloid solution of 0.2 mM prepared by a citric acid reduction method and allowed to shake for 3 days. Then, unadsorbed Py-g-PEG-Lactose was removed by ultracentrifugal separation (50,000 rpm, 10 minutes), and precipitated gold nanoparticles were cleaned with PBS buffer solution (150 mM NaCl) by repeating 3 cycles of ultracentrifugal separation (50,000 rpm, 10 minutes), thereby preparing gold nanoparticles coated with Py-g-PEG-Lactose. RCA 120 lectin of 20 µg/ml (manufactured by WAKO Co.) which is a lectin specifically recognizing galactose or 50 µg/ml of Con A (manufactured by Cosmo Bio Co.) which is a lectin specifically recognizing mannose was added to the dispersion of the gold nanoparticles, and aggregation of the gold nanoparticles coated with Py-g-PEG-Lactose was evaluated based on change of UV maximum absorption wavelength (see FIG. 18). Here, Con A was added to the dispersion of the gold nanoparticles coated with Py-g-PEG-Lactose (A) (A' in FIG. 18). UV spectra were measured using an ultraviolet-visible absorption spectrophotometer (Agilent 8453A Diod Array, manufactured by Agilent Co.).

The gold nanoparticles coated with Py-g-PEG-Lactose were initially in a dispersed state but agglomerated with time by addition of RCA 120 lectin. Furthermore, aggregation was higher as the rate of Hetero-PEG having an azide group, which is a functional group necessary for introducing lactose, was higher (A to D). In contrast, those added with Con A did not exhibit aggregation (A'). In addition, those containing no Hetero-PEG did not exhibit aggregation (E) (not shown).

The invention claimed is:

1. A graft copolymer between a polymerizable monomer A1 represented by general formula (III) and a polymerizable monomer B1 represented by the general formula (V),

(III)

in the formula, $R^{1a}$ represents a polymerizable group, $R^{2a}$ represents an alkylene group having a carbon number of 2-5, $R^{3a}$ represents an organic group having at a terminus a functional group selected from among an azide group, a phenyl azide group, a carboxyl group, a primary to quaternary amino group, an acetal group, an aldehyde group, a thiol group, a disulfide group, an active ester group, a trialkoxysilyl group, and a polymerizable group, and n represents any integer from 5 to 20,000,

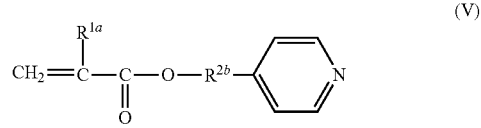

(V)

in the formula, $R^{1b}$ represents a hydrogen atom or an alkyl group having a carbon number of 1-10, and $R^{2b}$ represents an alkylene group having a carbon number of 3-5.

2. The graft copolymer according to claim 1, wherein the mole ratio of the polymerizable monomer A1 to the polymerizable monomer B1 is from 1:99 to 99:1.

3. The graft copolymer according to claim 1, wherein a ligand is bonded via the functional group at the terminus of $R^{3a}$ in general formula (III).

4. An object which has been modified by adsorbing on a surface thereof the graft copolymer according to claim 1.

5. A dispersion of nanoparticles, comprising nanoparticles surface-modified by adsorbing thereon the graft copolymer according to claim 1.

6. A method for producing nanoparticles, the method comprising using hydrophobic cores of micelles formed from the graft copolymer according to claim 1 as a reaction field.

7. A surface modifier, comprising a graft copolymer of a polymerizable monomer A2 having a group represented by general formula (VI) and a polymerizable monomer B2 having a repeating structure represented by general formula (VII)

(VI)

(VII)

in the formula, $R^a$ represents an alkylene group having a carbon number of 3-5, $R^b$ represents an alkylene group having a carbon number of 2-5, and n represents any integer from 5 to 2,000, wherein the polymerizable monomer A2 is represented by general formula (VIII)

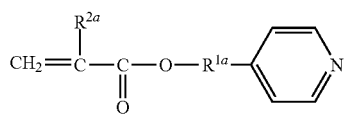

(VIII)

in the formula, $R^{1a}$ represents an alkylene group having a carbon number of 3-5, and $R^{2a}$ represents a hydrogen atom or a methyl group.

8. The surface modifier according to claim 7, wherein the polymerizable monomer B2 is represented by general formula (IX)

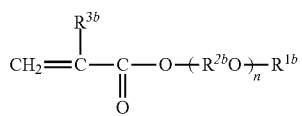

(IX)

in the formula, $R^{1b}$ represents a hydrogen atom or an alkyl group having a carbon number of 1-10, $R^{2b}$ represents an alkylene group having a carbon number of 2-5, $R^{3b}$ represents a hydrogen atom or a methyl group, and n represents any integer from 5 to 2,000.

9. The surface modifier according to claim 7, wherein the polymerizable monomer B2 has a weight-average molecular weight from 200 to 80,000.

10. The surface modifier according to claim 7, wherein the mole ratio of the polymerizable monomer A2 to the polymerizable monomer B2 is from 1:99 to 99:1.

11. An object which has been modified by adsorbing on a surface thereof the surface modifier according to claim 7.

12. A dispersion of nanoparticles, comprising nanoparticles surface-modified by adsorbing thereon the surface modifier according to claim 7.

13. A method for producing nanoparticles, the method comprising using hydrophobic cores of micelles formed from the surface modifier according to claim 7.

* * * * *